US008633158B1

(12) United States Patent
Franklin

(10) Patent No.: US 8,633,158 B1
(45) Date of Patent: Jan. 21, 2014

(54) ANGIOTENSIN IN TREATING BRAIN CONDITIONS

(71) Applicant: Tarix Pharmaceuticals Ltd., Cambridge, MA (US)

(72) Inventor: Richard Franklin, Cambridge, MA (US)

(73) Assignee: Tarix Pharmaceuticals Ltd., Cambridge, MA (US)

( * ) Notice: Subject to any disclaimer, the term of this patent is extended or adjusted under 35 U.S.C. 154(b) by 0 days.

(21) Appl. No.: 13/752,202

(22) Filed: Jan. 28, 2013

Related U.S. Application Data

(60) Provisional application No. 61/708,793, filed on Oct. 2, 2012, provisional application No. 61/720,299, filed on Oct. 30, 2012.

(51) Int. Cl.
*A61K 38/03* (2006.01)
*C07K 5/12* (2006.01)
*C07K 4/00* (2006.01)
*A61K 38/08* (2006.01)
*A61K 38/12* (2006.01)

(52) U.S. Cl.
USPC .............................. 514/9.7; 514/2.1; 530/300

(58) Field of Classification Search
None
See application file for complete search history.

(56) References Cited

U.S. PATENT DOCUMENTS

| | | | |
|---|---|---|---|
| 5,629,292 A | 5/1997 | Rodgers et al. |
| 5,716,935 A | 2/1998 | Rodgers et al. |
| 5,834,432 A | 11/1998 | Rodgers et al. |
| 5,955,430 A | 9/1999 | Rodgers et al. |
| 6,096,709 A | 8/2000 | Rodgers et al. |
| 6,110,895 A | 8/2000 | Rodgers et al. |
| 6,177,407 B1 | 1/2001 | Rodgers et al. |
| 6,239,109 B1 | 5/2001 | Rodgers et al. |
| 6,248,587 B1 | 6/2001 | Rodgers et al. |
| 6,258,778 B1 | 7/2001 | Rodgers et al. |
| 6,335,195 B1 | 1/2002 | Rodgers et al. |
| 6,444,646 B1 | 9/2002 | Rodgers et al. |
| 6,455,500 B1 | 9/2002 | Rodgers et al. |
| 6,475,988 B1 | 11/2002 | Rodgers et al. |
| 6,482,800 B1 | 11/2002 | Rodgers et al. |
| 6,498,138 B1 | 12/2002 | Rodgers et al. |
| 6,566,335 B1 | 5/2003 | Rodgers et al. |
| 6,730,775 B1 | 5/2004 | Rodgers et al. |
| 6,747,008 B1 | 6/2004 | Rodgers et al. |
| 6,762,167 B1 | 7/2004 | Rodgers et al. |
| 6,821,953 B1 | 11/2004 | Rodgers et al. |
| 6,916,783 B2 | 7/2005 | Rodgers et al. |
| 7,118,748 B1 | 10/2006 | Rodgers et al. |
| 7,122,523 B2 | 10/2006 | Rodgers et al. |
| 7,173,011 B2 | 2/2007 | Rodgers et al. |
| 7,176,183 B2 | 2/2007 | Rodgers et al. |
| 7,288,522 B1 | 10/2007 | Rodgers et al. |
| 7,338,938 B2 | 3/2008 | Rodgers et al. |
| 7,744,927 B2 | 6/2010 | Rodgers et al. |
| 7,745,411 B2 | 6/2010 | Rodgers et al. |
| 7,776,828 B2 | 8/2010 | Rodgers et al. |
| 7,786,085 B2 | 8/2010 | Rodgers et al. |
| 2002/0077344 A1 | 6/2002 | Heitsch et al. |
| 2008/0312129 A1* | 12/2008 | Souza Dos Santos et al. ... 514/2 |
| 2009/0227507 A1 | 9/2009 | Rodgers et al. |
| 2010/0316624 A1 | 12/2010 | Loibner et al. |
| 2011/0020315 A1 | 1/2011 | Loibner et al. |
| 2011/0033524 A1 | 2/2011 | Janzek-hawlat et al. |

FOREIGN PATENT DOCUMENTS

| | | |
|---|---|---|
| AU | 723373 B2 | 8/2000 |
| CA | 2205092 A1 | 5/1996 |
| CA | 2221730 A1 | 12/1996 |
| EP | 0914828 A2 | 5/1999 |
| EP | 2163259 A1 | 3/2010 |
| SU | 1067796 A1 | 1/1986 |
| WO | WO-95/08565 A1 | 3/1995 |
| WO | WO-96/14858 A1 | 5/1996 |
| WO | WO-96/39164 A1 | 12/1996 |
| WO | WO-98/26795 A1 | 6/1998 |
| WO | WO-98/32457 A2 | 7/1998 |
| WO | WO-99/10205 A1 | 3/1999 |
| WO | WO-99/26644 A1 | 6/1999 |
| WO | WO-99/40106 A2 | 8/1999 |
| WO | WO-99/45945 A1 | 9/1999 |
| WO | WO-99/46285 A2 | 9/1999 |
| WO | WO-99/52540 A1 | 10/1999 |
| WO | WO-00/02905 A2 | 1/2000 |
| WO | WO-00/09144 A1 | 2/2000 |
| WO | WO-00/56345 A2 | 9/2000 |
| WO | WO-01/43761 A2 | 6/2001 |
| WO | WO-01/98325 A1 | 12/2001 |
| WO | WO-02/87504 A2 | 11/2002 |
| WO | WO-03/039434 A2 | 5/2003 |

(Continued)

OTHER PUBLICATIONS

Pasut et al (Exp Opin Ther Pat: 14: 859-894, 2004).*
Ciobica et al (Acta Neurol Belg 109: 171-180, 2009).*
Ebermann L. et al., The angiotensin-(1-7) receptor agonist AVE0991 is cardioprotective in diabetic rats, European Journal of Pharmacology, 590:276-280 (2008).
Fang H.J. et al., Tissue-specific Pattern of Angiotensin-converting Enzyme 2 Expression in Rat Pancreas, The Journal of International Medical Research, 38:558-569 (2010).
Jiang, T. et al., Suppressing inflammation by inhibiting the NF-kB pathway contributes to the neuroprotective effect of angiotensin-(1-7) in rats with permanent cerebral ischaemia, British Journal of Pharmacology, 167(7):1520-1532 (2012).

(Continued)

Primary Examiner — Daniel E Kolker
Assistant Examiner — Aditi Dutt
(74) Attorney, Agent, or Firm — Choate, Hall & Stewart LLP; Fangli Chen; Brian E. Reese

(57) ABSTRACT

The present invention provides, among other things, methods and compositions for treating brain conditions. In some embodiments, the methods include administering to a subject suffering from or susceptible to a brain condition an angiotensin (1-7) peptide via either an intravenous or subcutaneous route of administration.

21 Claims, 9 Drawing Sheets

(56) References Cited

FOREIGN PATENT DOCUMENTS

| WO | WO-2007/000036 A2 | 1/2007 |
| WO | WO-2008/018792 A2 | 2/2008 |
| WO | WO-2009/114461 A2 | 9/2009 |
| WO | WO-2010/028845 A2 | 3/2010 |

OTHER PUBLICATIONS

Mecca, A.P. et al., Cerebroprotection by angiotensin-(1-7) in endothelin-1-induced ischaemic stroke, Experimental Physiology, 96(10):1084-1096 (2011).

Mocco, J. et al., Overexpression of Angiotensin (1-7) in Hematopoietic Stem Cells: A Novel Route of Delivery in Stroke, Presentation No. LB P21, Feb. 1, 2012.

Regenhardt, R.W. et al., Angiotensin (1-7) has therapeutic potential in hemorrhagic stroke, Physiology, University of Florida, Gainesville, FL, USA, Presentation Abstract No. 1049, May 25-28, 2011.

Regenhardt, R.W. et al., Angiotensin (1-7) reduces cerebral cortical iNOS expression in ischemic stroke: Possible mechanism for cerebroprotection?, Presentation Abstract, Program#/Poster#: 658.7/Q9, 40th Annual Meeting Neuroscience 2010, Nov. 16, 2010.

Soto-Pantoja, D.R. et al., Angiotensin-(1-7) inhibits tumor angiogenesis in human lung cancer xenografts with a reduction in vascular endothelial growth factor, Molecular Cancer Therapeutics, 8(6):1676-1683 (2009).

Santos, Robson, A.S., Pharmacological Effects of AVE 0991, a Nonpeptide Angiotensin-(1-7) Receptor Agonist, Cardiovascular Drug Reviews, 24(3-4):239-246 (2006).

Dharmani, M. et al., Effects of angiotensin 1-7 on the actions of angiotensin II in the renal and mesenteric vasculature of hypertensive and streptozotocin-induced diabetic rats, Eur. J. Pharmacol., Abstract only, 561(1-3):144-150 (2007).

Fraga-Silva, R.A. et al., ACE2 Activation Promotes Antithrombotic Activity, Mol. Med., 16(5-6):210-215 (2010).

Fraga-Silva, R.A. et al., The Antithrombotic Effect of Angiotensin-(1-7) Involves Mas-Mediated NO Release from Platelets, J. Mol. Med., 14(1-2):28-35 (2008).

Kluskens, L.D. et al., Angiotensin-(1-7) with Thioether Bridge: An Angiotensin-Converting Enzyme-Resistant, Potent Angiotensin-(1-7) Analog, J. Pharmacol. Exp. Ther., 328(3):849-854 (2009).

Machado, R.D.P. et al., Mechanisms of angiotensin-(1-7)-induced inhibition of angiogenesis, Am. J. Physiol. Regulatory Integrative Comp. Physiol., 280(4):R994-R1000 (2001).

Pardridge, W.M., The Blood-Brain Barrier: Bottleneck in Brain Drug Development, J. Am. Soc. Experimental NeuroTherapeutics, 2(1):3-14 (2005).

Rabelo, L.A. et al., ACE2-angiotensin-(1-7)-Mas axis and oxidative stress in cardiovascular disease, Hypertens. Res., 34(2):154-160, Abstract only (2011).

Regenhardt, R.W., Understanding the Cerebroprotective Actions of the ACE2/ANG-(1-7)Mas Axis During Ischemic and Hemorrhagic Stroke, a dissertation, University of Florida, 146 pages (2012).

Varagic, J. et al, New angiotensins, J. Mol. Med. (Berl), 86(6):663-671 (2008).

\* cited by examiner

ANGIOTENSIN IN TREATING BRAIN CONDITIONS

CROSS-REFERENCE TO RELATED APPLICATIONS

This application claim priority from U.S. provisional patent application Ser. No. 61/708,793, filed Oct. 2, 2012, U.S. provisional patent application Ser. No. 61/720,299, filed Oct. 30, 2012, the disclosures of which are hereby incorporated in their entirety.

SEQUENCE LISTING

The present specification makes reference to a Sequence Listing submitted electronically as a .txt file named "2009912-0053_ST25" on Jan. 28, 2012. The .txt file was generated on Jan. 28, 2013 and is 11 kb in size. The entire contents of the Sequence Listing are herein incorporated by reference.

BACKGROUND

Proper functioning of the central nervous system is essential in any animal. Damage to the brain in particular, such as through an ischemic or hemorrhagic stroke, can have dramatic and potentially deadly effects. One obstacle to treatment or prevention of brain damaging events is the blood brain barrier, which is a collection of tight junctions between neighboring capillary endothelial cells of the brain. These junctions prevent most substances from crossing unless they are either highly lipophilic or specifically transported across the blood brain barrier. As a result, it is extremely difficult to administer therapeutics via traditionally preferred routes, such as through an intravenous or subcutaneous administration and observe a therapeutic effect in the brain.

SUMMARY OF THE INVENTION

The present invention provides, among other things, methods and compositions for treating brain conditions including, but not limited to: stroke, vascular dementia, and traumatic brain injury. As described in the Examples section below, the present invention is, in part, based on the surprising discovery that systemic administration, such as subcutaneous administration, of an angiotensin (1-7) peptide (e.g., PanCyte), results in improvement of neurological and motor function in a rat model of ischemic stroke. Prior to the present invention, it was believed that angiotensin(1-7) would not cross the blood brain barrier and thus had to be administered intracerebrovascularly (ICV) or using complex methods such as infection of hematopoietic stem cells, which are capable of crossing the blood brain barrier, with a lentivirus that causes overexpression of Ang(1-7). Mecca et al., Cerebroprotection by Angiotensin-(1-7) in Endothelin-1-Induced Ischaemic Stroke, (2011) Exp Physiol. 2011 96(10):1084-1096. No one had shown that administration of an angiotensin (1-7) peptide or a non-peptidic Angiotensin-(1-7) agonist via a systemic (for example, either a subcutaneous or intravenous) route could result in therapeutic levels reaching the brain and, in particular, damaged brain tissue.

In some embodiments, the invention provides methods of treating a brain condition including administering to a subject suffering from or susceptible to a brain condition an angiotensin (1-7) peptide via systemic administration. In some embodiments, systemic administration suitable for the present invention is intravenous administration. In some embodiments, systemic administration suitable for the present invention is subcutaneous administration. In some embodiments, systemic administration suitable for the present invention is oral administration. In some embodiments, systemic administration suitable for the present invention does not include intracerebroventricular administration. In some embodiments, the brain condition is selected from stroke, vascular dementia, and traumatic brain injury. In some embodiments, the stroke is ischemic stroke. In some embodiments, the stroke is hemorrhagic stroke.

In some embodiments, the angiotensin (1-7) peptide is administered via continuous infusion. In some embodiments, the angiotensin (1-7) peptide is administered at an administration interval. For example, the angiotensin (1-7) peptide may be administered three times a day, twice a day, once per day, twice per week, once per week, three times per month, twice per month, once every two weeks, once every three weeks, once every four weeks, once a month, once every two months, once every three months, once every four months, once every five months, once every six months, at an irregular interval.

It is contemplated that various embodiments may use different amounts of angiotensin (1-7) peptide. In some embodiments, the angiotensin (1-7) peptide is administered at an effective dose ranging from about 1-1,000 µg/kg/day (e.g., ranging from about 1-900 µg/kg/day, 1-800 µg/kg/day, 1-700 µg/kg/day, 1-600 µg/kg/day, 1-500 µg/kg/day, 1-400 µg/kg/day, 1-300 µg/kg/day, 1-200 µg/kg/day, 1-100 µg/kg/day, 1-90 µg/kg/day, 1-80 µg/kg/day, 1-70 µg/kg/day, 1-60 µg/kg/day, 1-50 µg/kg/day, 1-40 µg/kg/day, 1-30 µg/kg/day, 1-20 µg/kg/day, 1-10 µg/kg/day). In some embodiments, the angiotensin (1-7) peptide is administered at an effective dose ranging from about 1-500 µg/kg/day. In some embodiments, the angiotensin (1-7) peptide is administered at an effective dose ranging from about 1-100 µg/kg/day. In some embodiments, the angiotensin (1-7) peptide is administered at an effective dose ranging from about 1-60 µg/kg/day. In some embodiments, the angiotensin (1-7) peptide is administered at an effective dose selected from about 1, 2, 4, 6, 8, 10, 15, 20, 25, 30, 35, 40, 45, 50, 75, 100, 150, 200, 250, 300, 350, 400, 450, 500, 550, 600, 650, 700, 750, 800, 850, 900, 950, or 1,000 ug/kg/day.

It is also contemplated that various angiotensin (1-7) peptides may be used in various embodiments. In some embodiments, the angiotensin (1-7) peptide comprises the naturally-occurring Angiotensin (1-7) amino acid sequence of $Asp^1$-$Arg^2$-$Val^3$-$Tyr^4$-$Ile^5$-$His^6$-$Pro^7$ (SEQ ID NO:1).

In some embodiments, the angiotensin (1-7) peptide is a functional equivalent of SEQ ID NO:1. In some embodiments, the functional equivalent is a linear peptide. In some embodiments, the linear peptide comprises a sequence that includes at least four, at least five, or at least six amino acids from the seven amino acids that appear in the naturally-occurring Angiotensin (1-7), wherein the at least four, five or six amino acids maintain their relative positions as they appear in the naturally-occurring Angiotensin (1-7). In some embodiments, the linear peptide contains 4-25 amino acids. In some embodiments, the linear peptide is a fragment of the naturally-occurring Angiotensin (1-7). In some embodiments, the linear peptide contains amino acid substitutions, deletions and/or insertions in the naturally-occurring Angiotensin (1-7). In some embodiments, the linear peptide has an amino acid sequence of $Asp^1$-$Arg^2$-$Val^3$-$ser^4$-$Ile^5$-$His^6$-$Cys^7$ (SEQ ID NO:2).

In some embodiments, the functional equivalent is a cyclic peptide. In some embodiments, the cyclic peptide comprises a linkage between amino acids. In some embodiments, the linkage is located at residues corresponding to positions $Tyr^4$ and $Pro^7$ in naturally-occurring Angiotensin (1-7). In some embodiments, the linkage is a thioether bridge. In some embodiments, the cyclic peptide comprises an amino acid sequence otherwise identical to the naturally-occurring Angiotensin (1-7) amino acid sequence of $Asp^1$-$Arg^2$-$Val^3$-$Tyr^4$-$Ile^5$-$His^6$-$Pro^7$ (SEQ ID NO:1). In some embodiments, the cyclic peptide comprises a norleucine (Nle) replacing position $Val^3$ in naturally-occurring Angiotensin (1-7). In some embodiments, the cyclic peptide is a 4,7-cyclized angiotensin (1-7) with the following formula $Asp^1$-$Arg^2$-$Val^3$-$Ser^4$-$Ile^5$-$His^6$-$Cys^7$ (SEQ ID NO: 22). In some embodiments, the cyclic peptide is a 4,7-cyclized angiotensin (1-7) with the following formula:

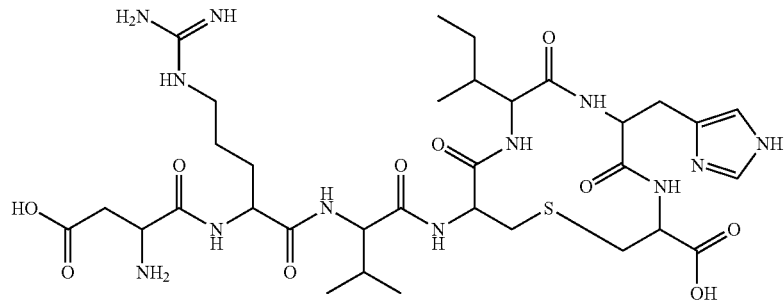 [SMILES: CCC(C)C1NC(=O)C(NC(=O)C(NC(=O)C(CCCNC(=N)N)NC(=O)C(N)CC(=O)O)C(C)C)CSCC(C(=O)O)NC(=O)C(Cc2c[nH]cn2)NC1=O]

In some embodiments, the angiotensin (1-7) peptide comprises one or more chemical modifications to increase protease resistance, serum stability and/or bioavailability. In some embodiments, the one or more chemical modifications comprise pegylation.

In some embodiments, the present invention provides methods of treating brain conditions including, but not limited to: stroke, vascular dementia, and traumatic brain injury including administering to a subject who is suffering from or susceptible to one or more brain conditions an angiotensin (1-7) receptor agonist. In some embodiments, the angiotensin (1-7) receptor agonist is a non-peptidic agonist. In some embodiments, the non-peptidic agonist is a compound with the following structure:

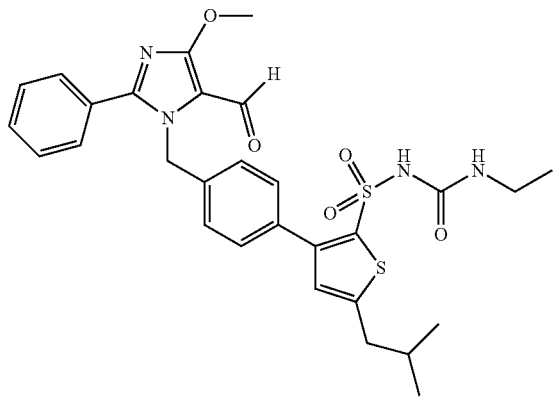 [SMILES: CCNC(=O)NS(=O)(=O)c1sc(CC(C)C)cc1-c1ccc(Cn2c(-c3ccccc3)nc(OC)c2C=O)cc1]

or a pharmaceutically acceptable salt thereof.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

DEFINITIONS

Figure 1:
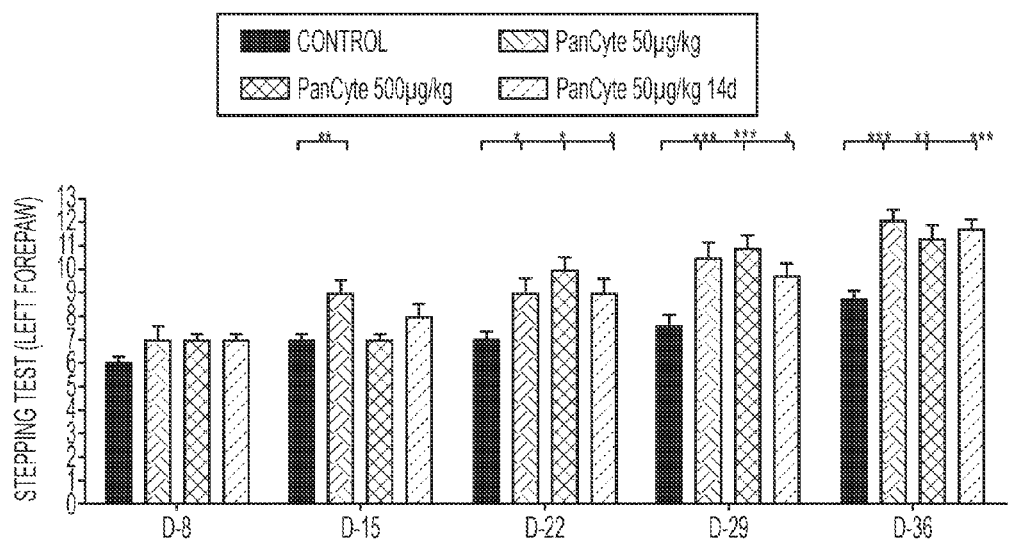
FIG. 1 shows an exemplary bar graph comparing the results of a step test administered on rats who received a transient middle cerebral arterial occlusion and either some amount of PanCyte for 14 or 49 days.

In order for the present invention to be more readily understood, certain terms are first defined below. Additional definitions for the following terms and other terms are set forth throughout the specification.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a peptide is biologically active, a portion of that peptide that shares at least one biological activity of the peptide is typically referred to as a "biologically active" portion. In certain embodiments, a peptide has no intrinsic biological activity but that inhibits the effects of one or more naturally-occurring angiotensin compounds is considered to be biologically active.

Brain Condition—as used herein, a "brain condition" is any disease, disorder or event that results in damage and/or dysfunction of at least a portion of a subject's brain. Non-limiting examples of brain conditions include: stroke (both ischemic and hemorrhagic), vascular dementia, and traumatic brain injury.

Carrier or diluent: As used herein, the terms "carrier" and "diluent" refers to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

Dosage form: As used herein, the terms "dosage form" and "unit dosage form" refer to a physically discrete unit of a therapeutic agent for the patient to be treated. Each unit contains a predetermined quantity of active material calculated to produce the desired therapeutic effect. It will be understood, however, that the total dosage of the composition will be decided by the attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses. In some embodiments, the therapeutic agent is administered continuously over a predetermined period. In some embodiments, the therapeutic agent is administered once a day (QD) or twice a day (BID).

Functional equivalent or derivative: As used herein, the term "functional equivalent" or "functional derivative" denotes, in the context of a functional derivative of an amino acid sequence, a molecule that retains a biological activity (either function or structural) that is substantially similar to that of the original sequence. A functional derivative or equivalent may be a natural derivative or is prepared synthetically. Exemplary functional derivatives include amino acid sequences having substitutions, deletions, or additions of one or more amino acids, provided that the biological activity of the protein is conserved. The substituting amino acid desirably has chemico-physical properties which are similar to that of the substituted amino acid. Desirable similar chemico-physical properties include, similarities in charge, bulkiness, hydrophobicity, hydrophilicity, and the like.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Prevent: As used herein, the term "prevent" or "prevention", when used in connection with the occurrence of a disease, disorder, and/or condition, refers to reducing the risk of developing the disease, disorder and/or condition. See the definition of "risk."

Polypeptide: The term "polypeptide" as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Risk: As will be understood from context, a "risk" of a disease, disorder, and/or condition comprises a likelihood that a particular individual will develop a disease, disorder, and/or condition (e.g., stroke). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., stroke). In some embodiments a reference sample or group of reference samples are from individuals comparable to a particular individual. In some embodiments, relative risk is 0, 1, 2, 3, 4, 5, 6, 7, 8, 9, 10, or more.

Stability: As used herein, the term "stable" refers to the ability of the therapeutic agent to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In certain embodiments, pharmaceutical compositions described herein have been formulated such that they are capable of stabilizing, or alternatively slowing or preventing the degradation, of one or more therapeutic agents formulated therewith. In the context of a formulation a stable formulation is one in which the therapeutic agent therein essentially retains its physical and/or chemical integrity and biological activity upon storage and during processes (such as freeze/thaw, mechanical mixing and lyophilization).

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, condition, or event (for example, ischemic stroke) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, condition, and/or event (5) having undergone, planning to undergo, or requiring a transplant. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION OF CERTAIN EMBODIMENTS

The present invention provides, among other things, improved compositions and methods for treating or reducing the risk of brain conditions resulting from damage to or disorder of brain tissue.

Various aspects of the invention are described in detail in the following sections. The use of sections is not meant to limit the invention. Each section can apply to any aspect of the invention. In this application, the use of "or" means "and/or" unless stated otherwise.

Brain Conditions

Stroke

The brain is highly vulnerable to a disturbance in its oxygen supply. Anoxia and ischemia lasting only a few seconds can cause symptoms and if the condition persists for minutes, they can cause irreversible neuronal damage. Accordingly, stroke is a prominent cause of serious, long-term disability and a leading cause of death in the United States. Stroke is also a significant burden on the medical industry, with total health costs for disability due to stroke being estimated at approximately $53 billion annually.

There are two types of stroke: ischemic and hemorrhagic. Ischemic stroke involves an obstruction in one or more blood vessels that supply blood to brain tissue, for example, occlusion resulting from atherosclerotic thrombii, or embolism. Ischemic stroke (cerebral ischemia) represent approximately 88% of all strokes, making ischemic stroke one of the most common types of cerebrovascular injury. Ischemic conditions in the brain quickly lead to neuronal death, often leading to permanent sensorimotor deficits. A hemorrhagic stroke is defined herein as the accumulation of blood anywhere within the cranial vault. Hemorrhagic strokes may result from many causes, including injury resulting from an expanding hematoma, which can disrupt or distort tissue.

A major barrier in the treatment of both ischemic and hemorrhagic stroke is delivery of a therapeutic that will reach affected tissue. Given the effectiveness of the blood brain barrier, few compounds are capable of crossing into and affecting cerebral tissue. Previously, delivery of compounds such as angiotensin (1-7), had to be made using intracerebroventricular (ICV) delivery. Surprisingly, embodiments of the present invention, including the exemplary angiotensin (1-7) peptides described below, are able to cross the blood brain barrier without complex delivery systems such as modified stem cells or the like. Rather, in some embodiments, angiotensin (1-7) peptides may be delivered via intravenous or subcutaneous routes.

Vascular Dementia

Vascular dementia is the second most common form of dementia, behind Alzheimer's Disease. Vascular dementia may result from problems with blood supply in the brain, such as those caused by ischemic or hemorrhagic stroke or from other causes that lead to development of lesions in the brain. Other causes of vascular dementia include cerebral amyloid angiopathy, hypercholesterolemia, diabetes mellitus, or cardiovascular disease. Dementia resulting from one or more strokes is also known as "single-infarct dementia" or "multi-infarct dementia," depending upon the root cause.

Treatment of vascular dementia has primarily focused on the prevention of further cerebrovascular lesions through use of antiplatelet drugs and life style changes (alteration of diet, cessation of smoking, etc). Cholinesterase inhibitors such as galantamine have also been explored for use in this clinical scenario, but this type of treatment is concerned with maintenance of acetylcholine function in the brain, and not recovery or generation of an improved and sustained blood supply. Thus, embodiments of the present invention represent a novel intravenous and subcutaneous therapy targeted to improving the underlying causes of the disease rather than management of symptoms or maximization of remaining tissue resources.

Traumatic Brain Injury

Traumatic brain injury (TBI), a form of acquired brain injury, occurs when a sudden trauma causes damage to the brain. TBI can result when the head suddenly and violently hits an object (or vice versa), or when an object pierces the skull and enters brain tissue. Symptoms of a TBI can be mild, moderate, or severe, depending on the extent of the damage to the brain. A person with a mild TBI may remain conscious or may experience a loss of consciousness for a few seconds or minutes. Other symptoms of mild TBI include headache, confusion, lightheadedness, dizziness, blurred vision or tired eyes, ringing in the ears, bad taste in the mouth, fatigue or lethargy, a change in sleep patterns, behavioral or mood changes, and trouble with memory, concentration, attention, or thinking. A person with a moderate or severe TBI may show these same symptoms, but may also have a headache that gets worse or does not go away, repeated vomiting or nausea, convulsions or seizures, an inability to awaken from sleep, dilation of one or both pupils of the eyes, slurred speech, weakness or numbness in the extremities, loss of coordination, and increased confusion, restlessness, or agitation.

Treatments for TBI focus primarily on preventing further injury or complications. Primary concerns in treating TBI include insuring proper oxygen supply to the brain and the rest of the body, maintaining adequate blood flow, and controlling blood pressure. Often, the primary treatment a TBI sufferer receives post-stabilization is rehabilitation that involves individually tailored treatment programs in the areas of physical therapy, occupational therapy, speech/language therapy, psychology/psychiatry, and social support. Embodiments of the present invention provide a novel treatment for these patients.

Angiotensin (1-7) Peptides

As used herein, the term "angiotensin (1-7) peptide" refers to both naturally-occurring Angiotensin (1-7) and any functional equivalent, analogue or derivative of naturally-occurring Angiotensin (1-7). As used herein, "peptide" and "polypeptide" are interchangeable terms and refer to two or more amino acids bound together by a peptide bond. As used herein, the terms "peptide" and "polypeptide" include both linear and cyclic peptide. The terms "angiotensin-(1-7)", "Angiotensin-(1-7)", and "Ang-(1-7)" are used interchangeably.

Naturally-Occurring Angiotensin (1-7)

Naturally-occurring Angiotensin (1-7) (also referred to as Ang-(1-7)) is a seven amino acid peptide shown below:

$Asp^1\text{-}Arg^2\text{-}Val^3\text{-}Tyr^4\text{-}Ile^5\text{-}His^6\text{-}Pro^7$ (SEQ ID NO:1)

It is part of the renin-angiotensin system and is converted from a precursor, also known as Angiotensinogen, which is an α-2-globulin that is produced constitutively and released into the circulation mainly by the liver. Angiotensinogen is a member of the serpin family and also known as renin substrate. Human angiotensinogen is 452 amino acids long, but other species have angiotensinogen of varying sizes. Typically, the first 12 amino acids are the most important for angiotensin activity:

$Asp^1\text{-}Arg^2\text{-}Val^3\text{-}Tyr^4\text{-}Ile^5\text{-}His^6\text{-}Pro^7\text{-}Phe^8\text{-}His^9\text{-}Leu^{10}\text{-}Val^{11}\text{-}Ile^{12}$ (SEQ ID NO:3)

Different types of angiotensin may be formed by the action of various enzymes. For example, Angiotensin (1-7) is generated by action of Angiotensin-converting enzyme 2 (ACE 2).

Ang-(1-7) is an endogenous ligand for Mas receptors. Mas receptors are G-protein coupled receptor containing seven transmembrane spanning regions. As used herein, the term "angiotensin-(1-7) receptor" encompasses the G Protein-Coupled Mas Receptors.

As used herein, the term "naturally-occurring Angiotensin (1-7)" includes any Angiotensin (1-7) peptide purified from natural sources and any recombinantly produced or chemically synthesized peptides that have an amino acid sequence identical to that of the naturally-occurring Angiotensin (1-7).

Functional Equivalents, Analogs or Derivatives of Ang-(1-7)

In some embodiments, an angiotensin (1-7) peptide suitable for the present invention is a functional equivalent of naturally-occurring Ang-(1-7). As used herein, a functional equivalent of naturally-occurring Ang-(1-7) refers to any peptide that shares amino acid sequence identity to the naturally-occurring Ang-(1-7) and retain substantially the same or similar activity as the naturally-occurring Ang-(1-7). For example, in some embodiments, a functional equivalent of naturally-occurring Ang-(1-7) described herein has pro-angiogenic activity as determined using methods described herein or known in the art, or an activity such as nitric oxide release, vasodilation, improved endothelial function, antidiuresis, or one of the other properties discussed herein, that positively impacts angiogenesis. In some embodiments, a functional equivalent of naturally-occurring Ang-(1-7) described herein can bind to or activate an angiotensin-(1-7) receptor (e.g., the G protein-coupled Mas receptor) as determined using various assays described herein or known in the art. In some embodiments, a functional equivalent of Ang-(1-7) is also referred to as an angiotensin (1-7) analogue or derivative, or functional derivative.

Typically, a functional equivalent of angiotensin (1-7) shares amino acid sequence similarity to the naturally-occurring Ang-(1-7). In some embodiments, a functional equivalent of Ang-(1-7) according to the invention contains a sequence that includes at least 3 (e.g., at least 4, at least 5, at least 6, at least 7) amino acids from the seven amino acids that appear in the naturally-occurring Ang-(1-7), wherein the at least 3 (e.g., at least 4, at least 5, at least 6, or at least 7) amino acids maintain their relative positions and/or spacing as they appear in the naturally-occurring Ang-(1-7).

In some embodiments, a functional equivalent of Ang-(1-7) also encompass any peptide that contain a sequence at least 50% (e.g., at least 60%, 70%, 80%, or 90%) identical to the amino acid sequence of naturally-occurring Ang-(1-7). Percentage of amino acid sequence identity can be determined by alignment of amino acid sequences. Alignment of amino acid sequences can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., Methods in Enzymology 266, 460-480 (1996); blast.wustl/edu/blast/README.html). WU-BLAST-2 uses several search parameters, most of which are set to the default values. The adjustable parameters are set with the following values: overlap span=1, overlap fraction=0.125, word threshold (T)=11. HSP score (S) and HSP S2 parameters are dynamic values and are established by the program itself, depending upon the composition of the particular sequence, however, the minimum values may be adjusted and are set as indicated above.

In some embodiments, a functional equivalent, analogue or derivative of Ang-(1-7) is a fragment of the naturally-occurring Ang-(1-7). In some embodiments, a functional equivalent, analogue or derivative of Ang-(1-7) contains amino acid substitutions, deletions and/or insertions in the naturally-occurring Ang-(1-7). Ang-(1-7) functional equivalents, analogues or derivatives can be made by altering the amino acid sequences by substitutions, additions, and/or deletions. For example, one or more amino acid residues within the sequence of the naturally-occurring Ang-(1-7) (SEQ ID NO:1) can be substituted by another amino acid of a similar polarity, which acts as a functional equivalent, resulting in a silent alteration. Substitution for an amino acid within the sequence may be selected from other members of the class to which the amino acid belongs. For example, the positively charged (basic) amino acids include arginine, lysine, and histidine. The nonpolar (hydrophobic) amino acids include leucine, isoleucine, alanine, phenylalanine, valine, proline, tryptophane, and methionine. The uncharged polar amino acids include serine, threonine, cysteine, tyrosine, asparagine, and glutamine. The negatively charged (acid) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions. For example, the amino acid sequence of a peptide inhibitor can be modified or substituted.

Examples of Ang-(1-7) functional equivalents, analogues and derivatives are described in the section entitled "Exemplary Angiotensin(1-7) Peptides" below.

An angiotensin-(1-7) peptide can be of any length. In some embodiments, an angiotensin-(1-7) peptide according to the present invention can contain, for example, from 4-25 amino acids (e.g., 4-20, 4-15, 4-14, 4-13, 4-12, 4-11, 4-10, 4-9, 4-8, 4-7 amino acids). In some embodiments, the linear peptide contains 4, 5, 6, 7, 8, 9, 10, 11, 12, 13, 14, 16, 17, 18, 19, 20, 21, 22, 23, 24, or 25 amino acids.

In some embodiments, an angiotensin-(1-7) peptide contains one or more modifications to increase protease resistance, serum stability and/or bioavailability. In some embodiments, suitable modifications are selected from pegylation, acetylation, glycosylation, biotinylation, substitution with D-amino acid and/or un-natural amino acid, and/or cyclization of the peptide.

As used herein, the term "amino acid," in its broadest sense, refers to any compound and/or substance that can be incorporated into a polypeptide chain. In certain embodiments, an amino acid has the general structure $H_2N$—$C(H)$(R)—COOH. In certain embodiments, an amino acid is a naturally-occurring amino acid. In certain embodiments, an amino acid is a synthetic or un-natural amino acid (e.g., α,α-disubstituted amino acids, N-alkyl amino acids); in some embodiments, an amino acid is a d-amino acid; in certain embodiments, an amino acid is an l-amino acid. "Standard amino acid" refers to any of the twenty standard amino acids commonly found in naturally occurring peptides including both l- and d-amino acids which are both incorporated in peptides in nature. "Nonstandard" or "unconventional amino acid" refers to any amino acid, other than the standard amino acids, regardless of whether it is prepared synthetically or obtained from a natural source. As used herein, "synthetic or un-natural amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical groups that can change the peptide's circulating half-life without adversely affecting its activity. Examples of unconventional or un-natural amino acids include, but are not limited to, citrulline, ornithine, norleucine, norvaline, 4-(E)-butenyl-4(R)-methyl-N-methylthreonine (MeBmt), N-methyl-leucine (MeLeu), aminoisobutyric acid, statine, and N-methyl-alanine (MeAla). Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

In certain embodiments, angiotensin-(1-7) peptides contain one or more L-amino acids, D-amino acids, and/or un-natural amino acids.

In addition to peptides containing only naturally occurring amino acids, peptidomimetics or peptide analogs are also encompassed by the present invention. Peptide analogs are commonly used in the pharmaceutical industry as non-peptide drugs with properties analogous to those of the template peptide. The non-peptide compounds are termed "peptide mimetics" or peptidomimetics (Fauchere et al., *Infect. Immun.* 54:283-287 (1986); Evans et al., *J. Med. Chem.* 30:1229-1239 (1987)). Peptide mimetics that are structurally related to therapeutically useful peptides and may be used to produce an equivalent or enhanced therapeutic or prophylactic effect. Generally, peptidomimetics are structurally similar to the paradigm polypeptide (i.e., a polypeptide that has a biological or pharmacological activity) such as naturally-occurring receptor-binding polypeptides, but have one or more peptide linkages optionally replaced by linkages such as $-CH_2NH-$, $-CH_2S-$, $-CH_2-CH_2-$, $-CH=CH-$ (cis and trans), $-CH_2SO-$, $-CH(OH)CH_2-$, $-COCH_2-$ etc., by methods well known in the art (Spatola, Peptide Backbone Modifications, Vega Data, 1(3):267 (1983); Spatola et al. *Life Sci.* 38:1243-1249 (1986); Hudson et al. *Int. J. Pept. Res.* 14:177-185 (1979); and Weinstein. B., 1983, Chemistry and Biochemistry, of Amino Acids, Peptides and Proteins, Weinstein eds, Marcel Dekker, New-York,). Such peptide mimetics may have significant advantages over naturally-occurring polypeptides including more economical production, greater chemical stability, enhanced pharmacological properties (e.g., half-life, absorption, potency, efficiency, etc.), reduced antigenicity and others.

Ang-(1-7) peptides also include other types of peptide derivatives containing additional chemical moieties not normally part of the peptide, provided that the derivative retains the desired functional activity of the peptide. Examples of such derivatives include (1) N-acyl derivatives of the amino terminal or of another free amino group, wherein the acyl group may be an alkanoyl group (e.g., acetyl, hexanoyl, octanoyl) an aroyl group (e.g., benzoyl) or a blocking group such as F-moc (fluorenylmethyl-O—CO—); (2) esters of the carboxy terminal or of another free carboxy or hydroxyl group; (3) amide of the carboxy-terminal or of another free carboxyl group produced by reaction with ammonia or with a suitable amine; (4) phosphorylated derivatives; (5) derivatives conjugated to an antibody or other biological ligand and other types of derivatives; and (6) derivatives conjugated to a polyethylene glycol (PEG) chain.

Ang-(1-7) peptides may be obtained by any method of peptide synthesis known to those skilled in the art, including synthetic (e.g., exclusive solid phase synthesis, partial solid phase synthesis, fragment condensation, classical solution synthesis, native-chemical ligation) and recombinant techniques. For example, the peptides or peptides derivatives can be obtained by solid phase peptide synthesis, which in brief, consist of coupling the carboxyl group of the C-terminal amino acid to a resin (e.g., benzhydrylamine resin, chloromethylated resin, hydroxymethyl resin) and successively adding N-alpha protected amino acids. The protecting groups may be any such groups known in the art. Before each new amino acid is added to the growing chain, the protecting group of the previous amino acid added to the chain is removed. Such solid phase synthesis has been disclosed, for example, by Merrifield, *J. Am. Chem. Soc.* 85: 2149 (1964); Vale et al., *Science* 213:1394-1397 (1981), in U.S. Pat. Nos. 4,305,872 and 4,316,891, Bodonsky et al. *Chem. Ind.* (London), 38:1597 (1966); and Pietta and Marshall, *Chem. Comm.* 650 (1970) by techniques reviewed in Lubell et al. "Peptides" Science of Synthesis 21.11, *Chemistry of Amides*. Thieme, Stuttgart, 713-809 (2005). The coupling of amino acids to appropriate resins is also well known in the art and has been disclosed in U.S. Pat. No. 4,244,946. (Reviewed in Houver-Weyl, *Methods of Organic Chemistry*. Vol E22a. Synthesis of Peptides and Peptidomimetics, Murray Goodman, Editor-in-Chief, Thieme. Stuttgart. New York 2002).

Unless defined otherwise, the scientific and technological terms and nomenclature used herein have the same meaning as commonly understood by a person of ordinary skill to which this invention pertains. Generally, the procedures of cell cultures, infection, molecular biology methods and the like are common methods used in the art. Such standard techniques can be found in reference manuals such as, for example, Ausubel et al., *Current Protocols in Molecular Biology*, Wiley Interscience, New York, 2001; and Sambrook et al., *Molecular Cloning: A Laboratory Manual*, $3^{rd}$ edition, Cold Spring Harbor Laboratory Press, N.Y., 2001.

During any process of the preparation of an Ang-(1-7) peptide, it may be desirable to protect sensitive reactive groups on any of the molecule concerned. This may be achieved by means of conventional protecting groups such as those described in Protective Groups In Organic Synthesis by T. W. Greene & P. G. M. Wuts, 1991, John Wiley and Sons, New-York; and Peptides: chemistry and Biology by Sewald and Jakubke, 2002, Wiley-VCH, Wheinheim p. 142. For example, alpha amino protecting groups include acyl type protecting groups (e.g., trifluoroacetyl, formyl, acetyl), aliphatic urethane protecting groups (e.g., t-butyloxycarbonyl (BOC), cyclohexyloxycarbonyl), aromatic urethane type protecting groups (e.g., fluorenyl-9-methoxy-carbonyl (Fmoc), benzyloxycarbonyl (Cbz), Cbz derivatives) and alkyl type protecting groups (e.g., triphenyl methyl, benzyl). The amino acids side chain protecting groups include benzyl (for Thr and Ser), Cbz (Tyr, Thr, Ser, Arg, Lys), methyl ethyl, cyclohexyl (Asp, His), Boc (Arg, His, Cys) etc. The protecting groups may be removed at a convenient subsequent stage using methods known in the art.

Further, Ang-(1-7) peptides may be synthesized according to the FMOC protocol in an organic phase with protective groups. Desirably, the peptides are purified with a yield of 70% with high-pressure liquid chromatography (HPLC) on a C18 chromatography column and eluted with an acetonitrile gradient of 10-60%. The molecular weight of a peptide can be verified by mass spectrometry (reviewed in Fields, G. B. "Solid-Phase Peptide Synthesis" *Methods in Enzymology*. Vol. 289, Academic Press, 1997).

Alternatively, Ang-(1-7) peptides may be prepared in recombinant systems using, for example, polynucleotide sequences encoding the polypeptides. It is understood that a polypeptide may contain more than one of the above-described modifications within the same polypeptide.

While peptides may be effective in eliciting a biological activity in vitro, their effectiveness in vivo might be reduced by the presence of proteases. Serum proteases have specific substrate requirements. The substrate must have both L-amino acids and peptide bonds for cleavage. Furthermore, exopeptidases, which represent the most prominent component of the protease activity in serum, usually act on the first peptide bond of the peptide and require a free N-terminus (Powell et al., *Pharm. Res.* 10:1268-1273 (1993)). In light of this, it is often advantageous to use modified versions of peptides. The modified peptides retain the structural characteristics of the original L-amino acid peptides that confer the desired biological activity of Ang-(1-7) but are advantageously not readily susceptible to cleavage by protease and/or exopeptidases.

Systematic substitution of one or more amino acids of a consensus sequence with D-amino acid of the same type (e.g., D-lysine in place of L-lysine) may be used to generate more stable peptides. Thus, a peptide derivative or peptidomimetic of the present invention may be all L, all D or mixed D, L peptide, in either forward or reverse order. The presence of an N-terminal or C-terminal D-amino acid increases the in vivo stability of a peptide since peptidases cannot utilize a D-amino acid as a substrate (Powell et al., *Pharm. Res.* 10:1268-1273 (1993)). Reverse-D peptides are peptides containing D-amino acids, arranged in a reverse sequence relative to a peptide containing L-amino acids. Thus, the C-terminal residue of an L-amino acid peptide becomes N-terminal for the D-amino acid peptide, and so forth. Reverse D-peptides retain the same secondary conformation and therefore similar activity, as the L-amino acid peptides, but are more resistant to enzymatic degradation in vitro and in vivo, and thus can have greater therapeutic efficacy than the original peptide (Brady and Dodson, *Nature* 368:692-693 (1994); Jameson et al., *Nature* 368:744-746 (1994)). Similarly, a reverse-L peptide may be generated using standard methods where the C-terminus of the parent peptide becomes takes the place of the N-terminus of the reverse-L peptide. It is contemplated that reverse L-peptides of L-amino acid peptides that do not have significant secondary structure (e.g., short peptides) retain the same spacing and conformation of the side chains of the L-amino acid peptide and therefore often have the similar activity as the original L-amino acid peptide. Moreover, a reverse peptide may contain a combination of L- and D-amino acids. The spacing between amino acids and the conformation of the side chains may be retained resulting in similar activity as the original L-amino acid peptide.

Another effective approach to confer resistance to peptidases acting on the N-terminal or C-terminal residues of a peptide is to add chemical groups at the peptide termini, such that the modified peptide is no longer a substrate for the peptidase. One such chemical modification is glycosylation of the peptides at either or both termini. Certain chemical modifications, in particular N-terminal glycosylation, have been shown to increase the stability of peptides in human serum (Powell et al., *Pharm. Res.* 10:1268-1273 (1993)). Other chemical modifications which enhance serum stability include, but are not limited to, the addition of an N-terminal alkyl group, consisting of a lower alkyl of from one to twenty carbons, such as an acetyl group, and/or the addition of a C-terminal amide or substituted amide group. In particular, the present invention includes modified peptides consisting of peptides bearing an N-terminal acetyl group and/or a C-terminal amide group.

Substitution of non-naturally-occurring amino acids for natural amino acids in a subsequence of the peptides can also confer resistance to proteolysis. Such a substitution can, for instance, confer resistance to proteolysis by exopeptidases acting on the N-terminus without affecting biological activity. Examples of non-naturally-occurring amino acids include α,α-disubstituted amino acids, N-alkyl amino acids, C-α-methyl amino acids, β-amino acids, and β-methyl amino acids. Amino acids analogs useful in the present invention may include, but are not limited to, β-alanine, norvaline, norleucine, 4-aminobutyric acid, orithine, hydroxyproline, sarcosine, citrulline, cysteic acid, cyclohexylalanine, 2-aminoisobutyric acid, 6-aminohexanoic acid, t-butylglycine, phenylglycine, o-phosphoserine, N-acetyl serine, N-formylmethionine, 3-methylhistidine and other unconventional amino acids. Furthermore, the synthesis of peptides with non-naturally-occurring amino acids is routine in the art.

In addition, constrained peptides comprising a consensus sequence or a substantially identical consensus sequence variation may be generated by methods well known in the art (Rizo and Gierasch, *Ann. Rev. Biochem.* 61:387-418 (1992)). For example, constrained peptides may be generated by adding cysteine residues capable of forming disulfide bridges and, thereby, resulting in a cyclic peptide. Cyclic peptides can be constructed to have no free N- or C-termini. Accordingly, they are not susceptible to proteolysis by exopeptidases, although they may be susceptible to endopeptidases, which do not cleave at peptide termini. The amino acid sequences of the peptides with N-terminal or C-terminal D-amino acids and of the cyclic peptides are usually identical to the sequences of the peptides to which they correspond, except for the presence of N-terminal or C-terminal D-amino acid residue, or their circular structure, respectively.

Cyclic Peptides

In some embodiments, a functional equivalent, analogue or derivative of naturally-occurring Ang-(1-7) is a cyclic peptide. As used herein, a cyclic peptide has an intramolecular covalent bond between two non-adjacent residues. The intramolecular bond may be a backbone to backbone, side-chain to backbone or side-chain to side-chain bond (i.e., terminal functional groups of a linear peptide and/or side-chain functional groups of a terminal or interior residue may be linked to achieve cyclization). Typical intramolecular bonds include disulfide, amide and thioether bonds. A variety of means for cyclizing polypeptides are well known in the art, as are many other modifications that can be made to such peptides. For a general discussion, see International Patent Publication Nos. WO 01/53331 and WO 98/02452, the contents of which are incorporated herein by reference. Such cyclic bonds and other modifications can also be applied to the cyclic peptides and derivative compounds of this invention.

Cyclic peptides as described herein may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. Cyclic peptides may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Suitable derivatives include amino acids having an N-acetyl group (such that the amino group that represents the N-terminus of the linear peptide prior to cyclization is acetylated) and/or a C-terminal amide group (i.e., the carboxy terminus of the linear peptide prior to cyclization is amidated). Residues other than common amino acids that may be present with a cyclic peptide include, but are not limited to, penicillamine, β,β-tetramethylene cysteine, β,β-pentamethylene cysteine, β-mercaptopropionic acid, β,β-pentamethylene-β-mercaptopropionic acid, 2-mercaptobenzene, 2-mercaptoaniline, 2-mercaptoproline, ornithine, diaminobutyric acid, α-aminoadipic acid, m-aminomethylbenzoic acid and α,β-diaminopropionic acid.

Following synthesis of a linear peptide, with or without N-acetylation and/or C-amidation, cyclization may be achieved by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Within further embodiments, cyclization may be achieved by amide bond formation. For example, a peptide bond may be formed between terminal functional groups (i.e., the amino and carboxy termini of a linear peptide prior to cyclization). Within another such embodiment, the linear peptide comprises a D-amino acid. Alternatively, cyclization may be accomplished by linking one terminus and a residue side chain or using two side chains, with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate. Methods for forming amide bonds are generally well known in the art. Within one such method, carbodiimide-mediated lactam formation can be accomplished by reaction of the carboxylic acid with DCC, DIC, EDAC or DCCl, resulting in the formation of an O-acylurea that can be reacted immediately with the free amino group to complete the cyclization. Alternatively, cyclization can be performed using the azide method, in which a reactive azide intermediate is generated from an alkyl ester via a hydrazide. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF.

Exemplary Angiotensin-(1-7) Peptides

In certain aspects, the invention provides linear angiotensin-(1-7) peptides. As discussed above, the structure of naturally-occurring Ang-(1-7) is as follows:

$Asp^1-Arg^2-Val^3-Tyr^4-Ile^5-His^6-Pro^7$ (SEQ ID NO:1)

The peptides and peptide analogs of the invention can be generally represented by the following sequence:

$Xaa^1-Xaa^2-Xaa^3-Xaa^4-Xaa^5-Xaa^6-Xaa^7$ (SEQ ID NO:4), or a pharmaceutically acceptable salt thereof.

$Xaa^1$ is any amino acid or a dicarboxylic acid. In certain embodiments, $Xaa^1$ is Asp, Glu, Asn, Acpc (1-aminocyclopentane carboxylic acid), Ala, $Me_2Gly$ (N,N-dimethylglycine), Pro, Bet (betaine, 1-carboxy-N,N,N-trimethylmethaninium hydroxide), Glu, Gly, Asp, Sar (sarcosine) or Suc (succinic acid). In certain such embodiments, $Xaa^1$ is a negatively-charged amino acid, such as Asp or Glu, typically Asp.

$Xaa^2$ is Arg, Lys, Ala, Cit (citrulline), Orn (ornithine), acetylated Ser, Sar, D-Arg and D-Lys. In certain embodiments, $Xaa^2$ is a positively-charged amino acid such as Arg or Lys, typically Arg.

$Xaa^3$ is Val, Ala, Leu, Nle (norleucine), Ile, Gly, Lys, Pro, HydroxyPro (hydroxyproline), Aib (2-aminoisobutyric acid), Acpc or Tyr. In certain embodiments, $Xaa^3$ is an aliphatic amino acid such as Val, Leu, Ile or Nle, typically Val or Nle.

$Xaa^4$ is Tyr, Tyr($PO_3$), Thr, Ser, homoSer (homoserine), azaTyr (aza-α¹-homo-L-tyrosine) or Ala. In certain embodiments, $Xaa^4$ is a hydroxyl-substituted amino acid such as Tyr, Ser or Thr, typically Tyr.

$Xaa^5$ is Ile, Ala, Leu, norLeu, Val or Gly. In certain embodiments, $Xaa^5$ is an aliphatic amino acid such as Val, Leu, Ile or Nle, typically Ile.

$Xaa^6$ is His, Arg or 6—$NH_2$-Phe (6-aminophenylalaine). In certain embodiments, $Xaa^6$ is a fully or partially positively-charged amino acid such as Arg or His.

$Xaa^7$ is Cys, Pro or Ala.

In certain embodiments, one or more of $Xaa^1-Xaa^7$ is identical to the corresponding amino acid in naturally-occurring Ang-(1-7). In certain such embodiments, all but one or two of $Xaa^1-Xaa^1$ are identical to the corresponding amino acid in naturally-occurring Ang-(1-7). In other embodiments, all of $Xaa^1-Xaa^6$ are identical to the corresponding amino acid in naturally-occurring Ang-(1-7).

In certain embodiments, $Xaa^3$ is Nle. When $Xaa^3$ is Nle, one or more of $Xaa^1-Xaa^2$ and $Xaa^{4-7}$ are optionally identical to the corresponding amino acid in naturally-occurring Ang-(1-7). In certain such embodiments, all but one or two of $Xaa^1-Xaa^2$ and $Xaa^{4-7}$ are identical to the corresponding amino acid in naturally-occurring Ang-(1-7). In other embodiments, all of $Xaa^1-Xaa^2$ and $Xaa^{4-7}$ are identical to the corresponding amino acid in naturally-occurring Ang-(1-7), resulting in the amino acid sequence: $Asp^1-Arg^2-Nle^3-Tyr^4-Ile^5-His^6-Pro^7$ (SEQ ID NO:5).

In certain embodiments, the peptide has the amino acid sequence $Asp^1-Arg^2-Val^3-Ser^4-Ile^5-His^6-Cys^7$ (SEQ ID NO:6) or $Asp^1-Arg^2-Val^3-ser^o-Ile^5-His^6-Cys^7$ (SEQ ID NO:2).

Exemplary Cyclic Angiotensin (1-7) Peptides

In certain aspects, the invention provides a cyclic angiotensin-(1-7) (Ang-(1-7)) peptide analog comprising a linkage, such as between the side chains of amino acids corresponding to positions $Tyr^4$ and $Pro^7$ in Ang. These peptide analogs typically comprise 7 amino acid residues, but can also include a cleavable sequence. As discussed in greater detail below, the invention includes fragments and analogs where one or more amino acids are substituted by another amino acid (including fragments). One example of such an analog is $Asp^1-Arg^2-Val^3-Ser^4-Ile^5-His^6-Cys^7$ (SEQ ID NO: 22), wherein a linkage is formed between $Ser^4$ and $Cys^7$.

Although the following section describes aspects of the invention in terms of a thioether bond linking residues at the 4- and 7-positions, it should be understood that other linkages (as described above) could replace the thioether bridge and that other residues could be cyclized. A thioether bridge is also referred to as a monosulfide bridge or, in the case of Ala-S-Ala, as a lanthionine bridge. Thioether bridge-containing peptides can be formed by two amino acids having one of the following formulas:

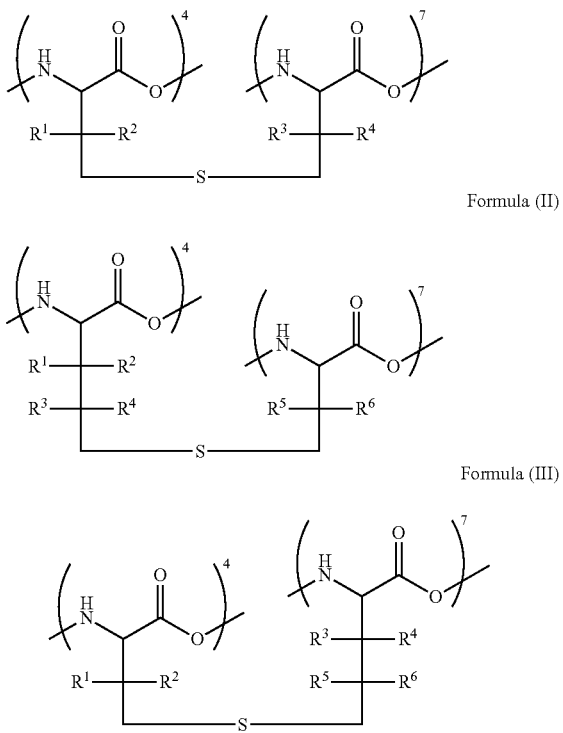

Formula (I)

Formula (II)

Formula (III)

In these formulae, $R^1$, $R^2$, $R^3$, $R^4$, $R^5$ and $R^6$ are independently —H, an alkyl (e.g., $C_1$-$C_6$ alkyl, $C_1$-$C_4$ alkyl) or an aralkyl group, where the alkyl and aralkyl groups are optionally substituted with one or more halogen, —OH or —NRR' groups (where R and R' are independently —H or $C_1$-$C_4$ alkyl). In certain embodiments, $R^1$, $R^2$, $R^3$, $R^4$, $R^5$ and $R^6$ are each independently —H or —$CH_3$, such where all are —H.

In certain embodiments, the invention provides an Ang analog or derivative comprising a thioether bridge according to formula (I). Typically, $R^1$, $R^2$, $R^3$ and $R^4$ are independently selected from —H and —$CH_3$. Peptides comprising a thioether bridge according to formula (I) can be produced, for example, by lantibiotic enzymes or by sulfur extrusion of a disulfide. In one example, the disulfide from which the sulfur is extruded can be formed by D-cysteine in position 4 and L-cysteine in position 7 or by D-cysteine in position 4 and L-penicillamine in position 7 (see, e.g., Galande, Trent and Spatola (2003) *Biopolymers* 71, 534-551).

In other embodiments, the linkage of the two amino acids can be the bridges depicted in Formula (II) or Formula (III). Peptides comprising a thioether bridge according to Formula (II) can be made, for example, by sulfur extrusion of a disulfide formed by D-homocysteine in position 4 and L-cysteine in position 7. Similarly, peptides comprising a thioether bridge as in Formula (III) can be made, for example, by sulfur extrusion of a disulfide formed by D-cysteine in position 4 and L-homocysteine in position 7.

As discussed above, the Ang analogs and derivatives of the invention vary in length and amino acid composition. The Ang analogs and derivatives of the invention preferably have biological activity or are an inactive precursor molecule that can be proteolytically activated (such as how angiotensin(I), with 10 amino acids, is converted to active fragments by cleavage of 2 amino acids). The size of an Ang analog or derivative can vary but is typically between from about 5 to 10 amino acids, as long as the "core" pentameric segment comprising the 3-7 Nle-thioether-ring structure is encompassed. The amino acid sequence of an analog or derivative of the invention can vary, typically provided that it is biologically active or can become proteolytically activated. Biological activity of an analog or derivative can be determined using methods known in the art, including radioligand binding studies, in vitro cell activation assays and in vivo experiments. See, for example, Godeny and Sayeski, (2006) *Am. J. Physiol. Cell. Physiol.* 291:C1297-1307; Sarr et al., *Cardiovasc. Res.* (2006) 71:794-802; and Koziarz et al., (1933) *Gen. Pharmacol.* 24:705-713.

Ang analogs and derivatives where only the length of the peptide is varied include the following:

a 4,7-cyclized analog designated [$Cyc^{4-7}$]Ang-(1-7), which is derived from natural Ang-(1-7) ($Asp^1$-$Arg^2$-$Val^3$-$Cyc^4$-$Ile^5$-$His^6$-$Cyc^7$, SEQ ID NO:7).

a 4,7-cyclized analog designated [$Nle^3$, $Cyc^{4-7}$]Ang-(1-10), which is derived from natural Angiotensin I (Ang-(1-10)) (Asp 1-$Arg^2$-$Nle^3$-$Cyc^4$-$Ile^5$-$His^6$-$Cyc^7$-$Phe^8$-$His^9$-$Leu^{10}$, SEQ ID NO:8);

a 4,7-cyclized analog designated [$Nle^3$, $Cyc^{4-7}$]Ang-(1-8), which is derived from natural Angiotensin II (Ang-(1-8)) ($Asp^1$-$Arg^2$-$Nle^3$-$Cyc^4$-$Ile^5$-$His^6$-$Cyc^7$-$Phe^8$, SEQ ID NO:9);

a 4,7-cyclised analog designated [$Nle^3$, $Cyc^{4-7}$]Ang-(2-8), which is derived from natural Angiotensin III (Ang-(2-8)) ($Arg^2$-$Nle^3$-$Cyc^4$-$Ile^5$-$His^6$-$Cyc^7$-$Phe^8$, SEQ ID NO:10);

a 4,7-cyclised analog designated [$Nle^3$, $Cyc^{4-7}$]Ang-(3-8), which is derived from natural Angiotensin IV (Ang-(3-8)) ($Nle^3$-$Cyc^4$-$Ile^5$-$His^6$-$Cyc^7$-$Phe^8$, SEQ ID NO:11);

a 4,7-cyclised analog designated [$Nle^3$, $Cyc^{4-7}$]Ang-(1-7) derived from natural Ang-(1-7) ($Asp^1$-$Arg^2$-$Nle^3$-$Cyc^4$-$Ile^5$-$His^6$-$Cyc^7$, SEQ ID NO:12); and a 4,7-cyclised analog designated [$Nle^3$, $Cyc^{4-7}$]Ang-(1-9) derived from natural Ang-(1-9) ($Asp^1$-$Arg^2$-$Nle^3$-$Cyc^4$-$Ile^5$-$His^6$-$Cyc^7$-$Phe^8$-$His^9$, SEQ ID NO:13).

These analogs can have one of the thioether bridges shown in Formulae (I)-(III) as the $Cyc^{4-7}$ moiety, for example, where $Cyc^4$ and $Cyc^7$ are represented by Formula (I), such as where $R^1$-$R^4$ are each —H or —$CH_3$, typically —H.

As compared to the amino acid sequence of the natural angiotensin peptide, the amino acids at positions 4 and 7 of the $Cyc^{4-7}$ analog are modified to allow introduction of the thioether-ring structures shown above. In addition to the length of the Ang analogs, the amino acids at positions other than 3, 4 and 7 can be the same or different from the naturally-occurring peptide, typically provided that the analog retains a biological function. For analogs of inactive precursors, like [$Cyc^{4-7}$]Ang-(1-10), biological function refers to one or both of an analog's susceptibility to angiotensin-converting enzymes that can cleave it to a biologically active fragment (e.g. Ang-(1-8) or Ang-(1-7)) or the biological activity of the fragment itself. In certain embodiments, an Ang analog or derivative of the invention has no intrinsic function but inhibits the effects of one or more naturally-occurring angiotensin compounds.

In certain embodiments, an Ang analog of the invention is represented by Formula (IV):

$Xaa^1$-$Xaa^2$-$Xaa^3$-$Cyc^4$-$Xaa^5$-$Xaa^6$-$Cyc^7$     (IV, SEQ ID NO:14)

$Xaa^1$ is any amino acid, but typically a negatively-charged amino acid such as Glu or Asp, more typically Asp.

$Xaa^2$ is a positively-charged amino acid such as Arg or Lys, typically Arg.

$Xaa^3$ is an aliphatic amino acid, such as Leu, Ile or Val, typically Val.

Cyc⁴ forms a thioether bridge in conjunction with Cyc⁷. Cyc⁴ can be a D-stereoisomer and/or a L-stereoisomer, typically a D-stereoisomer. Examples of Cyc⁴ (taken with Cyc⁷) are shown in Formulas (I), (II) and (III). Typically, the R groups in Formulae (I), (II) and (III) are —H or —CH₃, especially —H.

Xaa⁵ is an aliphatic amino acid, such as Leu, Ile or Val, typically Ile.

Xaa⁶ is His.

Cyc⁷ forms a thioether bridge in conjunction with Cyc⁴, such as in Formula (I), (II) or (III). Cyc⁷ can be a D-stereoisomer and/or a L-stereoisomer, typically a L-stereoisomer. Examples of Cyc⁷ (taken with Cyc⁴) are shown in Formulas (I), (II), (III) and (IV). Typically, the R groups in Formulae Formulas (I), (II),) and (III) and (IV) are —H or —CH₃, especially —H.

In certain embodiments, one or more of Xaa¹-Xaa⁶ (excluding Cyc⁴ and Cyc⁷) is identical to the corresponding amino acid in naturally-occurring Ang-(1-7). In certain such embodiments, all but one or two of Xaa¹-Xaa⁶ are identical to the corresponding amino acid in naturally-occurring Ang-(1-7). In other embodiments, all of Xaa¹-Xaa⁶ are identical to the corresponding amino acid in naturally-occurring Ang-(1-7).

In certain embodiments, Cyc⁴ and Cyc⁷ are independently selected from Abu (2-aminobutyric acid) and Ala (alanine), where Ala is present in at least one position. Thus, cyclic analogs can have a thioether linkage formed by -Ala⁴-S-Ala⁷- (Formula (I), where R¹-R⁴ are each —H); -Ala⁴-S-Abu⁷- (Formula (I): R¹-R³ are —H and R⁴ is —CH₃) or -Abu⁴-S-Ala⁷- (Formula (I): R¹, R³ and R⁴ are —H and R² is —CH₃). Specific examples of cyclic analogs comprise a -Abu⁴-S-Ala⁷- or -Ala⁴-S-Ala⁷- linkage.

In certain embodiments, the invention provides an Ang-(1-7) analog with a thioether-bridge between position 4 and position 7 having the amino acid sequence Asp¹-Arg²-Val³-Abu⁴-Ile⁵-His⁶-Ala⁷ (SEQ ID NO:15) or the amino acid sequence Asp¹-Arg²-Val³-Ala⁴-Ile⁵-His⁶-Ala⁷ (SEQ ID NO:16), which are represented by the following structural diagrams:

In certain embodiments, an Ang analog or derivative of the invention is represented by Formula (V):

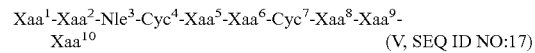

Xaa¹-Xaa²-Nle³-Cyc⁴-Xaa⁵-Xaa⁶-Cyc⁷-Xaa⁸-Xaa⁹-Xaa¹⁰             (V, SEQ ID NO:17)

As discussed above, one or more of Xaa¹, Xaa², Xaa⁸, Xaa⁹ and Xaa¹⁰ are absent in certain embodiments. For example, (1) Xaa¹⁰ is absent, (2) Xaa⁹ and Xaa¹⁰ are absent, (3) Xaa⁸, Xaa⁹ and Xaa¹⁰ are absent, (4) Xaa¹ is absent, (5) Xaa¹ and Xaa¹⁰ are absent, (6) Xaa¹, Xaa⁹ and Xaa¹⁰ are absent, (7) Xaa¹, Xaa⁸, Xaa⁹ and Xaa¹⁰ are absent, (8) Xaa¹ and Xaa² are absent, (9) Xaa¹, Xaa² and Xaa¹⁰ are absent, (10) Xaa¹, Xaa², Xaa⁹ and Xaa¹⁰ are absent, or (11) Xaa¹, Xaa², Xaa⁸, Xaa⁹ and Xaa¹⁰ are absent. For each of these embodiments, the remaining amino acids have the values described below.

Xaa¹, when present, is any amino acid, but typically a negatively charged amino acid such as Glu or Asp, more typically Asp.

Xaa², when present, is a positively charged amino acid such as Arg or Lys, typically Arg.

Nle³ is norleucine.

Cyc⁴ forms a thioether bridge in conjunction with Cyc⁷. Cyc⁴ can be a D-stereoisomer and/or a L-stereoisomer, typically a D-stereoisomer. Examples of Cyc⁴ (taken with Cyc⁷) are shown in Formulas (I), (II) and (III). Typically, the R groups in Formulae (I), (II) and (III) are —H or —CH₃, especially —H.

Xaa⁵ is an aliphatic amino acid, such as Leu, Nle, Ile or Val, typically Ile.

Xaa⁶ is His.

Cyc⁷ forms a thioether bridge in conjunction with Cyc⁴, such as in Formula (I), (II) or (III). Cyc⁷ can be a D-stereoisomer and/or a L-stereoisomer, typically a L-stereoisomer. Examples of Cyc⁷ (taken with Cyc⁴) are shown in Formulas (I), (II) and (III). Typically, the R groups in Formulae (I), (II) and (III) are —H or —CH₃, especially —H.

Xaa⁸, when present, is an amino acid other than Pro, typically Phe or Ile. In certain embodiments, Ile results in an

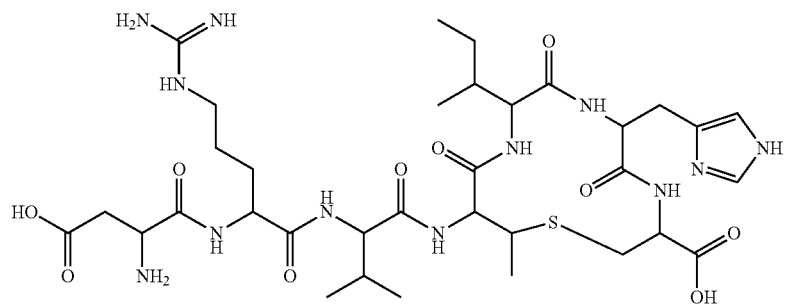

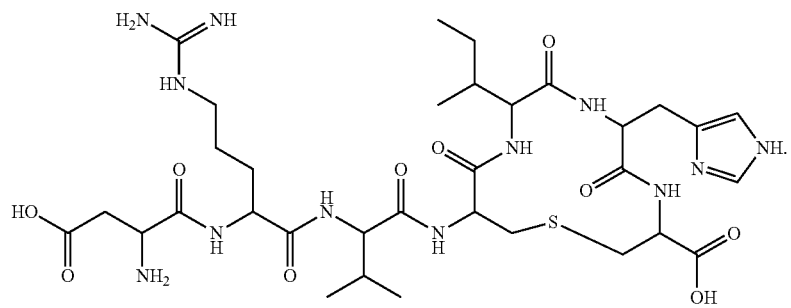

inhibitor of Ang(1-8). In certain embodiments, Phe maintains the biological activity of Ang(1-8) or Ang(1-10).

Xaa⁹, when present, is His.

Xaa¹⁰, when present, is an aliphatic residue, for example, Ile, Val or Leu, typically Leu.

In certain embodiments, one or more of Xaa¹-Xaa¹⁰ (excluding Nle³, Cyc⁴ and Cyc⁷) is identical to the corresponding amino acid in naturally-occurring Ang (including Ang-(1-7), Ang(1-8), Ang(1-9), Ang(1-10), Ang(2-7), Ang(2-8), Ang(2-9), Ang(2-10), Ang(3-8), Ang(3-9) and Ang(3-10). In certain such embodiments, all but one or two of Xaa¹-Xaa¹⁰ (for those present) are identical to the corresponding amino acid in naturally-occurring Ang. In other embodiments, all of Xaa¹-Xaa¹⁰ (for those present) are identical to the corresponding amino acid in naturally-occurring Ang.

In certain embodiments, Cyc⁴ and Cyc⁷ are independently selected from Abu (2-aminobutyric acid) and Ala (alanine), where Ala is present at at least one position. Thus, encompassed are cyclic analogs comprising a thioether linkage formed by -Ala⁴-S-Ala⁷- (Formula (I), where $R^1$-$R^4$ are each —H); -Ala⁴-S-Abu⁷- (Formula (I): $R^1$-$R^3$ are —H and $R^4$ is —CH₃) or -Abu⁴-S-Ala⁷- (Formula (I): $R^1$-$R^3$ and $R^4$ are —H and $R^2$ is —CH₃). Specific cyclic analogs comprise a -Abu⁴-S-Ala⁷- or -Ala⁴-S-Ala⁷- linkage.

In particular, the invention provides an Ang-(1-7) analog or derivative with a thioether-bridge between position 4 and position 7 having the amino acid sequence Asp¹-Arg²-Nle³-Abu⁴-Ile⁵-His⁶-Ala⁷ (SEQ ID NO:18) or the amino acid sequence Asp¹-Arg²-Nle³-Ala⁴-Ile⁵-His⁶-Ala⁷ (SEQ ID NO:19).

In another aspect, the invention provides an Ang-(1-8) analog or derivative with a thioether-bridge between position 4 and position 7 having Ang-(1-8) antagonistic activity, in particular an Ang(1-8) analog or derivative having the amino acid sequence Asp¹-Arg²-Nle³-Abu⁴-Ile⁵-His⁶-Ala⁷-Ile⁸ (SEQ ID NO:20), or the amino acid sequence Asp¹-Arg²-Nle³-Ala⁴-Ile⁵-His⁶-Ala⁷-Ile⁸ (SEQ ID NO:21).

An alkyl group is a straight chained or branched non-aromatic hydrocarbon that is completely saturated. Typically, a straight chained or branched alkyl group has from 1 to about 20 carbon atoms, preferably from 1 to about 10. Examples of straight chained and branched alkyl groups include methyl, ethyl, n-propyl, iso-propyl, n-butyl, sec-butyl, tert-butyl, pentyl, hexyl, pentyl and octyl. A C1-C4 straight chained or branched alkyl group is also referred to as a "lower alkyl" group.

An aralkyl group is an alkyl group substituted by an aryl group. Aromatic (aryl) groups include carbocyclic aromatic groups such as phenyl, naphthyl, and anthracyl, and heteroaryl groups such as imidazolyl, thienyl, furyl, pyridyl, pyrimidyl, pyranyl, pyrazolyl, pyrrolyl, pyrazinyl, thiazolyl, oxazolyl, and tetrazolyl. Aromatic groups also include fused polycyclic aromatic ring systems in which a carbocyclic aromatic ring or heteroaryl ring is fused to one or more other heteroaryl rings. Examples include benzothienyl, benzofuryl, indolyl, quinolinyl, benzothiazole, benzoxazole, benzimidazole, quinolinyl, isoquinolinyl and isoindolyl.

Ang (1-7) Receptor Agonists

In some embodiments, the present invention provides methods of treating brain conditions including administering to a subject who is suffering from or susceptible to one or more brain conditions an angiotensin (1-7) receptor agonist. As used herein, the term "angiotensin-(1-7) receptor agonist" encompasses any molecule that has a positive impact in a function of an angiotensin-(1-7) receptor, in particular the G-protein coupled Mas receptor. In some embodiments, an angiotensin-(1-7) receptor agonist directly or indirectly enhances, strengthens, activates and/or increases an angiotensin-(1-7) receptor (i.e., the Mas receptor) activity. In some embodiments, an angiotensin-(1-7) receptor agonist directly interacts with an angiotensin-(1-7) receptor (i.e., the Mas receptor). Such agonists can be peptidic or non-peptidic including, e.g., proteins, chemical compounds, small molecules, nucleic acids, antibodies, drugs, ligands, or other agents. In some embodiments, the angiotensin (1-7) receptor agonist is a non-peptidic agonist.

An exemplary class of angiotensin-(1-7) receptor agonists are 1-(p-thienylbenzyl)imidazoles. Examples of these non-peptide angiotensin-(1-7) receptor agonists are represented by Structural Formula (VI):

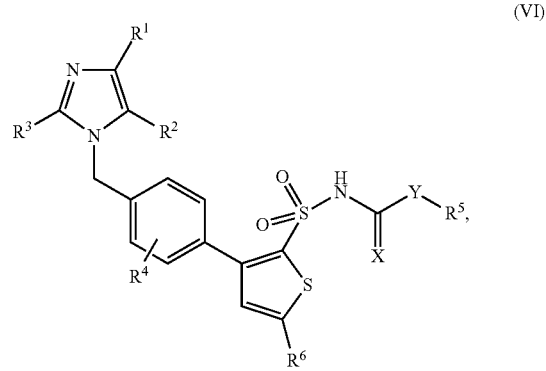

(VI)

or pharmaceutically acceptable salts thereof, wherein:

$R^1$ is halogen, hydroxyl, ($C_1$-$C_4$)-alkoxy, ($C_1$-$C_8$)-alkoxy wherein 1 to 6 carbon atoms are replaced by the heteroatoms O, S, or NH (preferably by O), ($C_1$-$C_4$)-alkoxy substituted by a saturated cyclic ether such as tetrahydropyran or tetrahydrofuran, O—($C_1$-$C_4$)-alkenyl, O—($C_1$-$C_4$)-alkylaryl, or aryloxy that is unsubstituted or substituted by a substituent selected from halogen, ($C_1$-$C_3$)-alkyl, ($C_1$-$C_3$)-alkoxy and trifluoromethyl;

$R^2$ is CHO, COOH, or (3) CO—O—($C_1$-$C_4$)-alkyl;

$R^3$ is ($C_1$-$C_4$)-alkyl or aryl;

$R^4$ is hydrogen, halogen (chloro, bromo, fluoro), or ($C_1$-$C_4$)-alkyl;

X is oxygen or sulfur;

Y is oxygen or —NH—;

$R^5$ is hydrogen, ($C_1$-$C_6$)-alkyl; or ($C_1$-$C_4$)-alkylaryl, where $R^5$ is hydrogen when Y is —NH—; and $R^6$ is ($C_1$-$C_5$)-alkyl.

In certain embodiments, $R^1$ is not halogen when $R^2$ is COOH or CO—O—($C_1$-$C_4$)-alkyl.

In some embodiments, an angiotensin-(1-7) receptor agonist is AVE 0991, 5-formyl-4-methoxy-2-phenyl-1[[4-[2-(ethylaminocarbonylsulfonamido)-5-isobutyl-3-thienyl]-phenyl]-methyl]-imidazole, which is represented by the following structure:

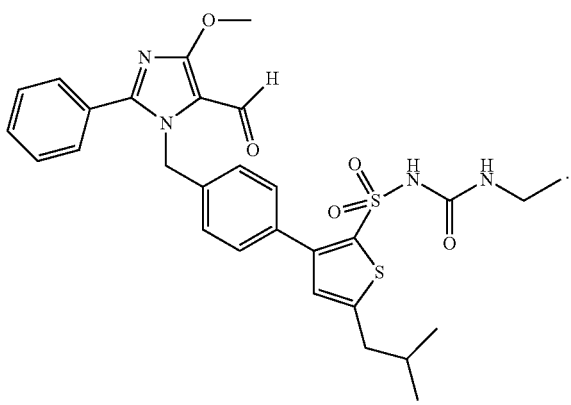 [SMILES: CCNC(=O)NS(=O)(=O)c1sc(CC(C)C)cc1-c1ccc(Cn2c(-c3ccccc3)nc(OC)c2C=O)cc1]

Another exemplary class of angiotensin-(1-7) receptor agonists are p-thienylbenzylamides. Examples of these non-peptide angiotensin-(1-7) receptor agonists are represented by Structural Formula (VII):

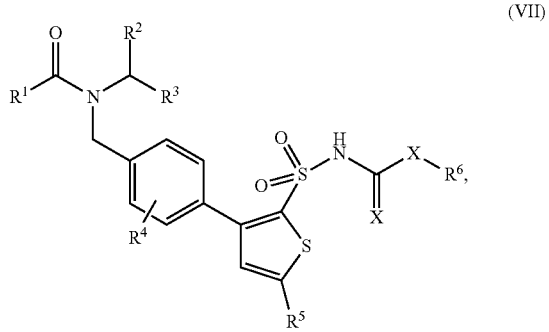

or a pharmaceutically acceptable salt thereof, wherein:

$R^1$ is $(C_1-C_5)$-alkyl that is unsubstituted or substituted by a radical chosen from $NH_2$, halogen, O—$(C_1-C_3)$-alkyl, CO—O—$(C_1-C_3)$-alkyl and $CO_2H$, $(C_3-C_8)$-cycloalkyl, $(C_1-C_3)$-alkyl-$(C_3-C_8)$-cycloalkyl, $(C_6-C_{10})$-aryl that is unsubstituted or substituted by a radical chosen from halogen and O—$(C_1-C_3)$-alkyl, $(C_1-C_3)$-alkyl-$(C_6-C_{10})$-aryl where the aryl radical is unsubstituted or substituted by a radical chosen from halogen and O—$(C_1-C_3)$-alkyl, $(C_1-C_5)$-heteroaryl, or $(C_1-C_3)$-alkyl-$(C_1-C_5)$-heteroaryl;

$R^2$ is hydrogen, $(C_1-C_6)$-alkyl that is unsubstituted or substituted by a radical chosen from halogen and O—$(C_1-C_3)$-alkyl, $(C_3-C_8)$-cycloalkyl, $(C_1-C_3)$-alkyl-$(C_3-C_8)$-cycloalkyl, $(C_6-C_{10})$-aryl that is unsubstituted or substituted by a radical chosen from among halogen, O—$(C_1-C_3)$-alkyl and CO—O—$(C_1-C_3)$-alkyl, or $(C_1-C_3)$-alkyl-$(C_6-C_{10})$-aryl that is unsubstituted or substituted by a radical chosen from halogen and O—$(C_1-C_3)$-alkyl;

$R^3$ is hydrogen, COOH, or COO—$(C_1-C_4)$-alkyl;

$R^4$ is hydrogen, halogen; or $(C_1-C_4)$-alkyl;

$R^5$ is hydrogen or $(C_1-C_6)$-alkyl;

$R^6$ is hydrogen, $(C_1-C_6)$-alkyl, $(C_1-C_3)$-alkyl-$(C_3-C_8)$-cycloalkyl, or $(C_2-C_6)$-alkenyl; and X is oxygen or NH.

Additional examples of angiotensin-(1-7) receptor agonists are described in U.S. Pat. No. 6,235,766, the contents of which are incorporated by reference herein.

Various angiotensin-(1-7) receptor agonists described above can be present as pharmaceutically acceptable salts. As used herein, "a pharmaceutically acceptable salt" refers to salts that retain the desired activity of the peptide or equivalent compound, but preferably do not detrimentally affect the activity of the peptide or other component of a system, which uses the peptide. Examples of such salts are acid addition salts formed with inorganic acids, for example, hydrochloric acid, hydrobromic acid, sulfuric acid, phosphoric acid, nitric acid, and the like. Salts may also be formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, and the like. Salts formed from a cationic material may utilize the conjugate base of these inorganic and organic acids. Salts may also be formed with polyvalent metal cations such as zinc, calcium, bismuth, barium, magnesium, aluminum, copper, cobalt, nickel and the like or with an organic cation formed from N,N'-dibenzylethylenediamine or ethylenediamine, or combinations thereof (e.g., a zinc tannate salt). The non-toxic, physiologically acceptable salts are preferred.

The salts can be formed by conventional means such as by reacting the free acid or free base forms of the product with one or more equivalents of the appropriate acid or base in a solvent or medium in which the salt is insoluble, or in a solvent such as water which is then removed in vacuo or by freeze-drying, or by exchanging the cations of an existing salt for another cation on a suitable ion exchange resin.

An alkyl group is a straight chained or branched non-aromatic hydrocarbon that is completely saturated. Typically, a straight chained or branched alkyl group has from 1 to about 20 carbon atoms, preferably from 1 to about 10. Examples of straight chained and branched alkyl groups include methyl, ethyl, n-propyl, iso-propyl, n-butyl, sec-butyl, tert-butyl, pentyl, hexyl, pentyl and octyl. A C1-C4 straight chained or branched alkyl group is also referred to as a "lower alkyl" group.

An alkenyl group is a straight chained or branched non-aromatic hydrocarbon that is includes one or more double bonds. Typically, a straight chained or branched alkenyl group has from 2 to about 20 carbon atoms, preferably from 2 to about 10. Examples of straight chained and branched alkenyl groups include ethenyl, n-propenyl, and n-butenyl.

Aromatic (aryl) groups include carbocyclic aromatic groups such as phenyl, naphthyl, and anthracyl, and heteroaryl groups such as imidazolyl, thienyl, furyl, pyridyl, pyrimidyl, pyranyl, pyrazolyl, pyrrolyl, pyrazinyl, thiazolyl, oxazolyl, and tetrazolyl. Aromatic groups also include fused polycyclic aromatic ring systems in which a carbocyclic aromatic ring or heteroaryl ring is fused to one or more other heteroaryl rings. Examples include benzothienyl, benzofuryl, indolyl, quinolinyl, benzothiazole, benzoxazole, benzimidazole, quinolinyl, isoquinolinyl and isoindolyl.

An aralkyl group is an alkyl group substituted by an aryl group.

Formulations

In accordance with the methods of the invention, an Ang (1-7) peptide or angiotensin (1-7) receptor agonist as described herein of the invention can be administered to a subject alone (e.g., as a purified peptide or compound), or as a component of a composition or medicament (e.g., in the manufacture of a medicament for the treatment of the disease), as described herein. The compositions can be formulated with a physiologically acceptable carrier or excipient to prepare a pharmaceutical composition. The carrier and composition can be sterile. The formulation should suit the mode of administration, for example intravenous or subcutaneous administration. Methods of formulating compositions are known in the art (see, e.g., Remington's Pharmaceuticals Sciences, 17th Edition, Mack Publishing Co., (Alfonso R. Gennaro, editor) (1989)).

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring and/or aromatic substances and the like) which do not deleteriously react with the active compounds or interference with their activity. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, sustained release formulation, or powder. The composition can also be formulated as a suppository, with traditional binders and carriers such as triglycerides.

The composition or medicament can be formulated in accordance with the routine procedures as a pharmaceutical composition adapted for administration to human beings. For example, in a preferred embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

An Ang (1-7) peptide or angiotensin (1-7) receptor agonist as described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

An Ang (1-7) peptide or angiotensin (1-7) receptor agonist as described herein (or a composition or medicament containing an Ang (1-7) peptide or angiotensin (1-7) receptor agonist described herein) is administered by any appropriate route. In some embodiments, an Ang (1-7) peptide or angiotensin (1-7) receptor agonist described herein is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region. In some embodiments, an Ang (1-7) peptide or angiotensin (1-7) receptor agonist described herein is administered intravenously. Alternatively, an Ang (1-7) peptide or angiotensin (1-7) receptor agonist described herein (or a composition or medicament containing an Ang (1-7) peptide or angiotensin (1-7) receptor agonist described herein) can be administered by inhalation, parenterally, intradermally, transdermally, rectally, or transmucosally. More than one route can be used concurrently, if desired.

In some embodiments, a composition is administered in a therapeutically effective amount and/or according to a dosing regimen that is correlated with a particular desired outcome (e.g., with treating or reducing risk for ischemic stroke).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill. In some embodiments, an appropriate dose or amount is determined in accordance with standard clinical techniques. For example, in some embodiments, an appropriate dose or amount is a dose or amount sufficient to reduce a disease severity index score by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100% or more. For example, in some embodiments, an appropriate dose or amount is a dose or amount sufficient to reduce a disease severity index score by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100%. Alternatively or additionally, in some embodiments, an appropriate dose or amount is determined through use of one or more in vitro or in vivo assays to help identify desirable or optimal dosage ranges or amounts to be administered.

In various embodiments, an Ang (1-7) peptide or angiotensin (1-7) receptor agonist is administered at a therapeutically effective amount. As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

Therapeutically effective dosage amounts of angiotensin (1-7) peptides or angiotensin (1-7) receptor agonists, including derivatives, analogs, and/or salts may be present in varying amounts in various embodiments. For example, in some embodiments, a therapeutically effective amount of an angiotensin (1-7) peptide may be an amount ranging from about 10-1000 mg (e.g., about 20 mg-1,000 mg, 30 mg-1,000 mg, 40 mg-1,000 mg, 50 mg-1,000 mg, 60 mg-1,000 mg, 70 mg-1,000 mg, 80 mg-1,000 mg, 90 mg-1,000 mg, about 10-900 mg, 10-800 mg, 10-700 mg, 10-600 mg, 10-500 mg, 100-1000 mg, 100-900 mg, 100-800 mg, 100-700 mg, 100-600 mg, 100-500 mg, 100-400 mg, 100-300 mg, 200-1000 mg, 200-900 mg, 200-800 mg, 200-700 mg, 200-600 mg, 200-500 mg, 200-400 mg, 300-1000 mg, 300-900 mg, 300-800 mg, 300-700 mg, 300-600 mg, 300-500 mg, 400 mg-1, 000 mg, 500 mg-1,000 mg, 100 mg-900 mg, 200 mg-800 mg, 300 mg-700 mg, 400 mg-700 mg, and 500 mg-600 mg). In some embodiments, an angiotensin (1-7) peptide or angiotensin (1-7) receptor agonist is present in an amount of or greater than about 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg. In some embodiments, an angiotensin (1-7) peptide or angiotensin (1-7) receptor agonist is present in an amount of or less than about 1000 mg, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, or 100 mg. In some embodiments, the therapeutically effective amount described herein is provided in one dose. In some embodiments, the therapeutically effective amount described herein is provided in one day.

In other embodiments, a therapeutically effective dosage amount may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight. In some embodiments, the therapeutically effective amount described herein is provided in one dose. In some embodiments, the therapeutically effective amount described herein is provided in one day.

In still other embodiments, a therapeutically effective dosage amount may be, for example, about 0.001 mg/kg weight to about 1 mg/kg weight, e.g. from about 0.001 mg/kg weight to about 0.9 mg/kg weight, from about 0.001 mg/kg weight to about 0.8 mg/kg weight, from about 0.001 mg/kg weight to about 0.8 mg/kg weight, from about 0.001 mg/kg weight to about 0.7 mg/kg weight, from about 0.001 mg/kg weight to about 0.6 mg/kg weight, from about 0.001 mg/kg weight to about 0.5 mg/kg weight, from about 0.01 mg/kg weight to about 1 mg/kg weight, from about 0.01 mg/kg weight to about 0.9 mg/kg weight, from about 0.01 mg/kg weight to about 0.8 mg/kg weight, from about 0.01 mg/kg weight to about 0.7 mg/kg weight, from about 0.01 mg/kg weight to about 0.6 mg/kg weight, from about 0.01 mg/kg weight to about 0.5 mg/kg weight, from about 0.02 mg/kg weight to about 1 mg/kg weight, from about 0.02 mg/kg weight to about 0.9 mg/kg weight, from about 0.02 mg/kg weight to about 0.8 mg/kg weight, from about 0.02 mg/kg weight to about 0.7 mg/kg weight, from about 0.02 mg/kg weight to about 0.6 mg/kg weight, from about 0.02 mg/kg weight to about 0.5 mg/kg weight, from about 0.03 mg/kg weight to about 1 mg/kg weight, from about 0.03 mg/kg weight to about 0.9 mg/kg weight, from about 0.03 mg/kg weight to about 0.8 mg/kg weight, from about 0.03 mg/kg weight to about 0.7 mg/kg weight, from about 0.03 mg/kg weight to about 0.6 mg/kg weight, from about 0.03 mg/kg weight to about 0.5 mg/kg weight, from about 0.04 mg/kg weight to about 1 mg/kg weight, from about 0.04 mg/kg weight to about 0.9 mg/kg weight, from about 0.04 mg/kg weight to about 0.8 mg/kg weight, from about 0.04 mg/kg weight to about 0.7 mg/kg weight, from about 0.04 mg/kg weight to about 0.6 mg/kg weight, from about 0.04 mg/kg weight to about 0.5 mg/kg weight, from about 0.05 mg/kg weight to about 1 mg/kg weight, from about 0.05 mg/kg weight to about 0.9 mg/kg weight, from about 0.05 mg/kg weight to about 0.8 mg/kg weight, from about 0.05 mg/kg weight to about 0.7 mg/kg weight, from about 0.05 mg/kg weight to about 0.6 mg/kg weight, from about 0.05 mg/kg weight to about 0.5 mg/kg weight. In some embodiments, the therapeutically effective amount described herein is provided in one dose. In some embodiments, the therapeutically effective amount described herein is provided in one day.

In still other embodiments, a therapeutically effective dosage amount may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual.

In some embodiments, the angiotensin (1-7) peptide is administered at an effective dose ranging from about 1-1,000 µg/kg/day (e.g., ranging from about 1-900 µg/kg/day, 1-800 µg/kg/day, 1-700 µg/kg/day, 1-600 µg/kg/day, 1-500 µg/kg/day, 1-400 µg/kg/day, 1-300 µg/kg/day, 1-200 µg/kg/day, 1-100 µg/kg/day, 1-90 µg/kg/day, 1-80 µg/kg/day, 1-70 µg/kg/day, 1-60 µg/kg/day, 1-50 µg/kg/day, 1-40 µg/kg/day, 1-30 µg/kg/day, 1-20 µg/kg/day, 1-10 µg/kg/day). In some embodiments, the angiotensin (1-7) peptide is administered at an effective dose ranging from about 1-500 µg/kg/day. In some embodiments, the angiotensin (1-7) peptide is administered at an effective dose ranging from about 1-100 µg/kg/day. In some embodiments, the angiotensin (1-7) peptide is administered at an effective dose ranging from about 1-60 µg/kg/day. In some embodiments, the angiotensin (1-7) peptide is administered at an effective dose selected from about 1, 2, 4, 6, 8, 10, 15, 20, 25, 30, 35, 40, 45, 50, 75, 100, 150, 200, 250, 300, 350, 400, 450, 500, 550, 600, 650, 700, 750, 800, 850, 900, 950, or 1,000 ug/kg/day.

Dosing Schedules

Various embodiments may include differing dosing regimen. In some embodiments, the angiotensin (1-7) peptide or angiotensin (1-7) receptor agonist is administered via continuous infusion. In some embodiments, the continuous infusion is intravenous. In other embodiments, the continuous infusion is subcutaneous. Alternatively or additionally, in some embodiments, the angiotensin (1-7) peptide or angiotensin (1-7) receptor agonist is administered bimonthly, monthly, twice monthly, triweekly, biweekly, weekly, twice weekly, thrice weekly, daily, twice daily, or on another clinically desirable dosing schedule. The dosing regimen for a single subject need not be at a fixed interval, but can be varied over time, depending on the needs of the subject.

Combination Therapies

In some embodiments, an Ang (1-7) peptide or angiotensin (1-7) receptor agonist will be used as a part of a combination therapy. It is contemplated that any known therapeutic or treatment for one or more brain conditions may be used with one or more Ang (1-7) peptides or angiotensin (1-7) receptor agonists as disclosed herein. Exemplary compounds that may be used with one or more Ang (1-7) peptides or angiotensin (1-7) receptor agonists as a combination therapy include, but are not limited to, thrombolytic compounds, antioxidants or other reactive oxygen species agents, interferon beta-1a (e.g. Avonex, Rebif, CinnoVex, ReciGen), interferon beta-1b (Betaseron), glatiramer acetate (Copaxone), mitoxantrone (Novantrone), natalizumab (Tysabri), fingolimod (Gilenya), the first oral drug available, and Teriflunomide (Aubagio), or combinations thereof.

Kits

In some embodiments, the present invention further provides kits or other articles of manufacture which contains an Ang (1-7) peptide, an angiotensin (1-7) receptor agonist or a formulation containing the same and provides instructions for its reconstitution (if lyophilized) and/or use. Kits or other articles of manufacture may include a container, a syringe, vial and any other articles, devices or equipment useful in administration (e.g., subcutaneous, by inhalation). Suitable containers include, for example, bottles, vials, syringes (e.g., pre-filled syringes), ampules, cartridges, reservoirs, or lyojects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may holds formulations and a label on, or associated with, the container that may indicate directions for reconstitution and/or use. For example, the label may indicate that the formulation is reconstituted to concentrations as described above. The label may further indicate that the formulation is useful or intended for, for example, subcutaneous administration. In some embodiments, a container may contain a single dose of a stable formulation containing an Ang (1-7) peptide or angiotensin (1-7) receptor agonist. In various embodiments, a single dose of the stable formulation is present in a volume of less than about 15 ml, 10 ml, 5.0 ml, 4.0 ml, 3.5 ml, 3.0 ml, 2.5 ml, 2.0 ml, 1.5 ml, 1.0 ml, or 0.5 ml. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least 1 mg/ml (e.g., at least 5 mg/ml, at least 10 mg/ml, at least 20 mg/ml, at least 30 mg/ml, at least 40 mg/ml, at least 50 mg/ml, at least 75 mg/ml, at least 100 mg/ml). Kits or other articles of manufacture may further include other materials desirable from a commercial and user standpoint, including other buffers, diluents, filters, needles, syringes, and package inserts with instructions for use. In some embodiments, kits or other articles of manufacture may include an instruction for self-administration.

EXAMPLES

Example 1

Continuous PanCyte Administration

Several animal models have been used to study cerebral ischemia in an effort to understand its pathophysiology and to identify therapeutic strategies for minimizing the severity of ischemic damage. Focal ischemia brings about localized brain infarction and may be induced by middle cerebral artery occlusion (MCAO). A rat model of MCAO has gained acceptance as a model for hemispheric infarction in humans. After MCAO, a cortical and striatal infarct with temporal and spatial evolution occurs within the vascular region supplied by the middle cerebral artery.

In the past several years, ample evidence has been gathered regarding behavioral assessments in stroke animal studies, including the MCAO rat model of ischemic stroke. Behavioral improvement is thought to be a reliable parameter for efficacy studies of potential therapeutics.

A desirable treatment for vascular complications of stroke would be a non-invasive means of promoting neovascularization in ischemic tissues. Embodiments of the present invention provide such a therapeutic treatment. Binding of angiotensin (1-7) peptides on the cell surface of endothelial cells can rescue those cells from apoptosis, induce their proliferation, migration, and formation of small blood vessels in vitro.

In this example, the MCAO rat model was used to evaluate the dose-dependent efficacy of angiotensin (1-7) peptides, for example, PanCyte, in improving post-occlusion function as measured by several accepted behavioral evaluations.

Animal handling was performed according to guidelines of the National Institute of Health (NIH) and the Association for Assessment and Accreditation of Laboratory Animal Care (AAALAC). Animals were housed in polyethylene cages (5/cage) measuring 35×30×15 cm, with stainless steel top grill facilitating pelleted food and drinking water in plastic bottle; bedding: steam sterilized clean paddy husk (Harlan, Sani-chip cat#:2018SC+F) was used and bedding material were changed along with the cage at least twice a week. In this example, a total of 60 rats were used and each rat weighed approximately 300 grams at study initiation.

Animals were fed ad libitum a commercial rodent diet (Teklad Certified Global 18% Protein Diet cat #: 106S8216). Animals had free access to acidified drinking water (pH between 2.5 and 3.5) obtained from the municipality supply according to PharmaSeed's SOP No. 214 (Water System). Animals were housed under standard laboratory conditions, air conditioned and filtered (HEPA F6/6) with adequate fresh air supply (Minimum 15 air changes/hour). Animals were kept in a climate controlled environment. Animals were kept within a temperatures range of approximately 20-24° C. with a relative humidity range of 30-70% and a 12 hours light-dark cycle. Animals were inspected on arrival and were inspected daily for any signs of morbidity or mortality. Animals found in a moribund condition and animals showing severe pain and enduring signs of severe distress (such as dyspnea, lateral recumbency, convulsions, plegia or inability to reach food or water) were humanely euthanized.

For the purposes of this example, Transient middle cerebral artery occlusion (tMCAO) procedure Day is defined as "Day 1" in this study. On the day of surgery anesthesia were induced with 4% isoflurane in a mixture of 70% $N_2O$ and 30% $O_2$ and maintained with 1.5-2% isoflurane.

The tMCAO procedures were performed according to the method described R. Schmid-Elsaesser et al. Briefly, the right CCA (Common Carotid Artery) was exposed through a midline neck incision and carefully dissected free from surrounding nerves and fascia—from its bifurcation to the base of the skull. The occipital artery branches of the ECA (External Carotid Artery) were then isolated, and these branches were dissected and coagulated. The ECA was dissected further distally and coagulated along with the terminal lingual and maxillary artery branches, which was then divided. The ICA (Internal Carotid Artery) was isolated and carefully separated from the adjacent vagus nerve, and the pterygopalatine artery was ligated close to its origin with a 5-0 nylon suture (SMI, Belgium). Next, a 4-0 silk suture was tied loosely around the mobilized ECA stump, and a 4 cm length of 4-0 monofilament nylon suture (the tip of the suture was blunted by using a flame, and the suture was coated with polylysine, prior to insertion) was inserted through the proximal ECA into the ICA and thence into the circle of Willis, effectively occluding the MCA. The surgical wound was closed and the animals were returned to their cages to recover from anesthesia. One hour and a half after occlusion rats were re-anesthetized, the monofilament was withdrawn to allow reperfusion, the surgical wound was closed and rats were returned to their cages.

Animals were subjected to a modified Modified Neurological Rating Scale (mNRS) at 24 hours post reperfusion. Only animals with an overall score of ≥10 are included in this study. Animals were allocated into the test groups, according to the mNRS results on day 2, in order to have similar distribution of rats performance between groups. Started on day 2, 24 hours post-surgery, each animal is implanted subcutaneously with osmotic Alzet pump and is treated by continuous PanCyte administration (2.5 mg/ml or 25 mg/ml in PBS; SEQ ID NO:22). See Table 1 for group allocation:

TABLE 1

Group Allocation

| Group | Treatment | Dose | Treatment duration (days) | Total rats |
|---|---|---|---|---|
| 1 | Vehicle | 0 | 49 | 15 |
| 2 | PanCyte | 50 µg/kg (2.5 mg/ml) | 49 | 15 |
| 3 | PanCyte | 500 µg/kg (25 mg/ml) | 49 | 15 |
| 4 | PanCyte | 50 µg/kg (2.5 mg/ml) | 14 | 15 |

Stepping Test (Evaluation at Day 8, Day 15, Day 22, Day 29 and Day 36)

Animals were tested for forelimb akinesia in a stepping test. The animal was held with its hind limbs fixed with one hand and the forelimb not monitored with the other, while the unrestrained fore-paw touches a table. The number of adjusting steps were counted while the animal was moved sideways along the table surface (85 cm in approximately five seconds), in the forehand & backhand direction for both forelimbs. FIG. 1 shows the results of the stepping test at days 8, 15, 22, 29 and 36. Four groups were analyzed in this test, a control group (receiving only PBS for 49 days), a group receiving 50 µg/kg PanCyte for 49 days, a group receiving 500 µg/kg PanCyte for 49 days, and a group receiving 50 µg/kg PanCyte for 14 days. The data shows that each group receiving administration of PanCyte enjoyed increased performance of rats by day 22 as compared to control animals, and that this effect continued through day 36, with increasing statistical significance. Additionally, the group that was exposed to 50 µg/kg dose of PanCyte for 49 days performed significantly better than controls on day 15 as well, while the groups exposed to either 500 µg/kg of PanCyte for 49 days or 50 µg/kg Pancyte for 14 days, while trending toward improvement, did not reach statistically significant levels at this time point in this particular experiment.

Forelimb Placement (Evaluation at Day 8, Day 15, Day 22, Day 29 and Day 36)

Figure 2:
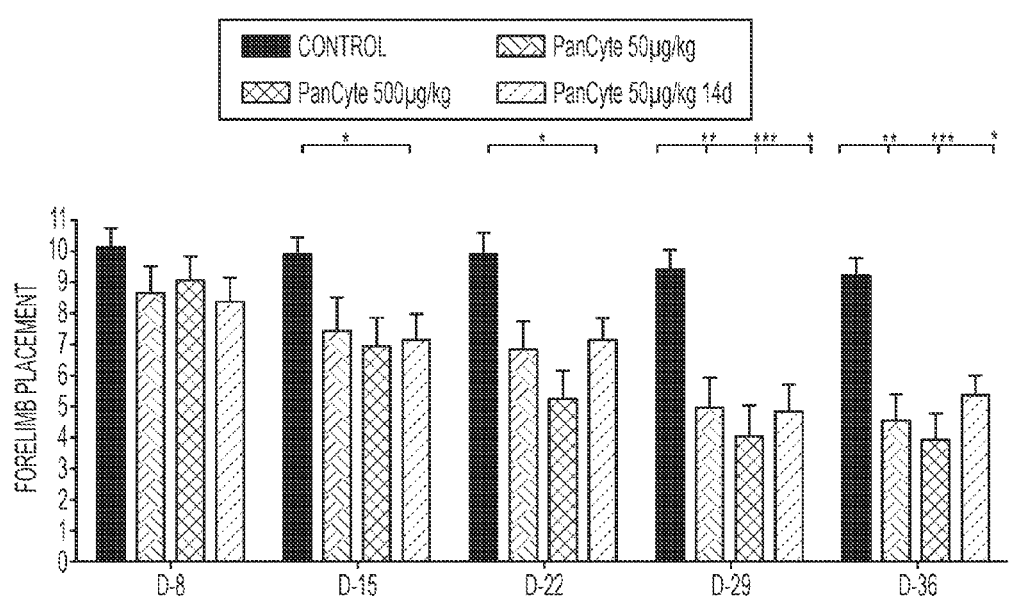
FIG. 2 shows an exemplary bar graph comparing the results of a forelimb placement test administered on rats who received a transient middle cerebral arterial occlusion and either some amount of PanCyte for 14 or 49 days.

The limb placing tests were divided into both forelimb and hindlimb tests. For the forelimb-placing test, the examiner held the rat close to a tabletop and scored the rat's ability to place the forelimb on the tabletop in response to whisker, visual, tactile, or proprioceptive stimulation. Similarly, for the hindlimb placing test, the examiner assessed the rat's ability to place the hindlimb on the tabletop in response to tactile and proprioceptive stimulation. Separate sub-scores were obtained for each mode of sensory input and added to give total scores (for the forelimb placing test: 0=normal, 12=maximally impaired; for the hindlimb placing test: 0=normal; 6=maximally impaired). Scores were given in half-point increments as follows: Forelimb placing test: whisker placing (0-2), visual placing—forward (0-2), -sideways (0-2); tactile placing—dorsal (0-2), -lateral (0-2); proprioceptive placing (0-2); for a total of 0-12. FIG. 2 shows the results of the forelimb placing test at days 8, 15, 22, 29 and 36. Four groups were analyzed in this test, a control group (receiving only PBS for 49 days), a group receiving 50 µg/kg PanCyte for 49 days, a group receiving 500 µg/kg PanCyte for 49 days, and a group receiving 50 µg/kg PanCyte for 14 days. The data shows that each group receiving administration of PanCyte enjoyed increased performance on this test by day 29 as compared to control animals, and that this effect continued to day 36. Also, the group exposed to 50 µg/kg Pancyte for 14 days performed significantly better than control animals beginning on day 15, whereas the other treatment groups, though trending in the same way, did not reach statistical significance until day 29 in this experiment.

Body Swing Test (Evaluation at Day 8, Day 15, Day 22, Day 29 and Day 36)

Figure 3:
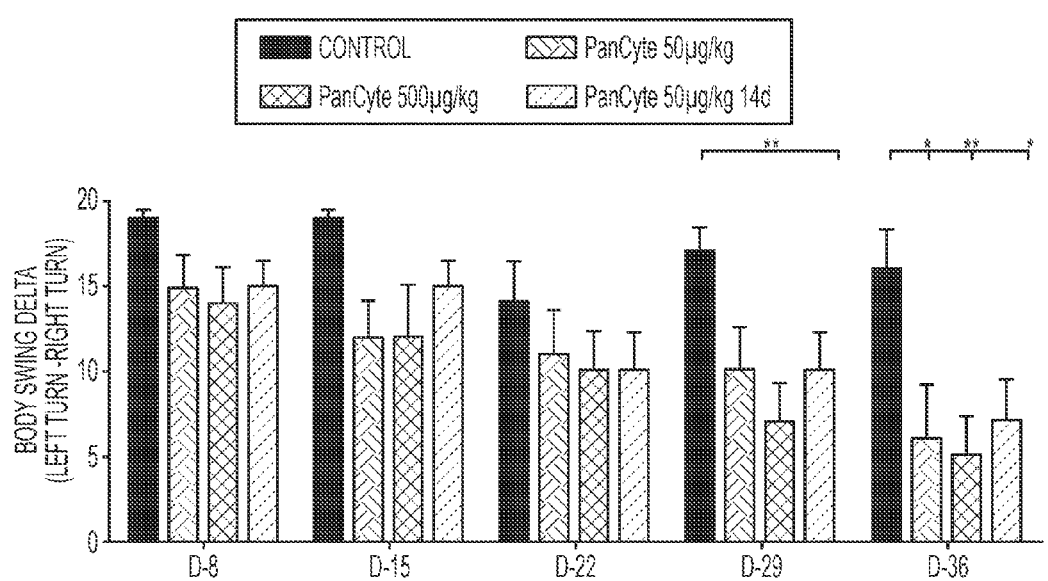
FIG. 3 shows an exemplary bar graph comparing the results of a body swing test administered on rats who received a transient middle cerebral arterial occlusion and either some amount of PanCyte for 14 or 49 days.

The rat was held approximately one inch from the base of its tail. It was then elevated to an inch above a surface of a table. The rat was held in the vertical axis, defined as no more than 10° to either the left or the right side. A swing was recorded whenever the rat moved its head out of the vertical axis to either side. Before attempting another swing, the rat had to return to the vertical position for the next swing to be counted. Twenty (20) total swings were counted. A normal rat typically has an equal number of swings to either side. Following focal ischemia, rats tend to swing to the contralateral side (left side in this example). Body swing scores are expressed as a percentage of rightward over total swings. FIG. 3 shows the results of the body swing test at days 8, 15, 22, 29 and 36. Four groups were analyzed in this test, a control group (receiving only PBS for 49 days), a group receiving 50 µg/kg PanCyte for 49 days, a group receiving 500 µg/kg PanCyte for 49 days, and a group receiving 50 µg/kg PanCyte for 14 days. The data shows that each group receiving administration of PanCyte enjoyed improved performance on the test by day 36 as compared to the control group, with the group receiving 50 µg/kg PanCyte for 14 days showed statistical significance beginning on day 29 as compared to control in this experiment. All treatment groups exhibited a trend toward improved scores beginning on day 8 as compared to the control group.

mNRS Evaluation (Evaluation at Day 1, Day 8, Day 15, Day 22, Day 29 and Day 36)

Figure 4:
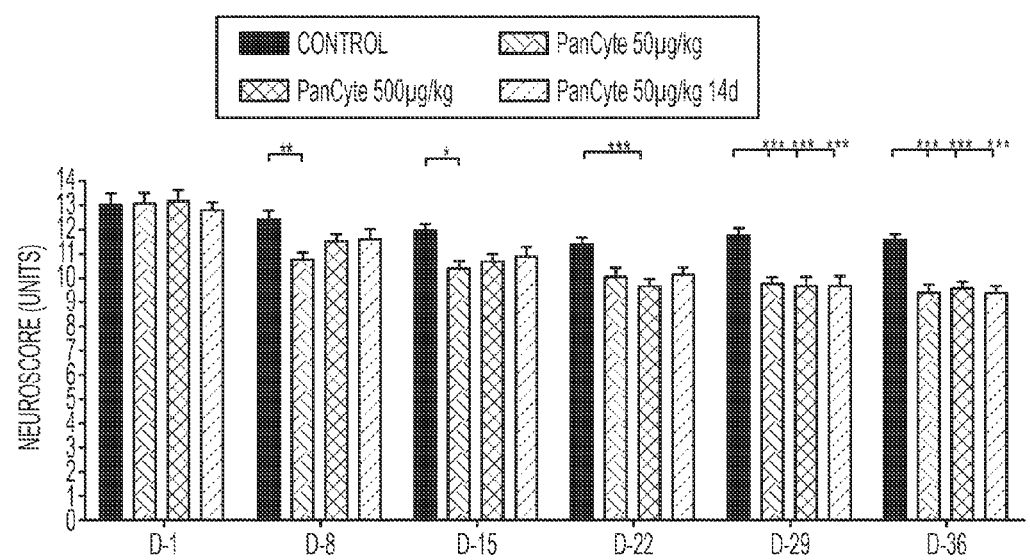
FIG. 4 shows an exemplary bar graph comparing the results of a neurological test (modified Neuroscore Scoring Scale) administered on rats who received a transient middle cerebral arterial occlusion and either some amount of PanCyte for 14 or 49 days.

The Modified Neurological Rating Scale (mNRS) was administered by an individual who was unaware of the drug/dose given (blind test). The mNRS as administered allows for neuro-scoring on a scale of 0 to 18 possible points. Animals with higher scores showed more severe symptoms and disability than lower scoring rats. FIG. 4 shows the results of the mNRS evaluation at days 1, 8, 15, 22, 29 and 36. Four groups were analyzed in this test, a control group (receiving only PBS for 49 days), a group receiving 50 µg/kg PanCyte for 49 days, a group receiving 500 µg/kg PanCyte for 49 days, and a group receiving 50 µg/kg PanCyte for 14 days. The data shows that each group receiving administration of PanCyte enjoyed improved performance on the test by day 29 as compared to the control group. In addition to days 29 and 36, the group receiving 50 µg/kg PanCyte for 49 days showed statistically improved performance on days 8 and 15, and the group receiving 500 µg/kg PanCyte for 49 days showed statistically improved performance on day 22 in this experiment.

Example 2

Comparison of TXA127, PanCyte, or Linear PanCyte Administration

The animal model, surgical procedures, and animal care procedures and conditions were as described above for Example 1 unless otherwise specified. In this example, a total of 105 animals were used, and Table 2 shows the group allocation for this study:

TABLE 2

Group Allocation

| Group | Treatment | Dose | Treatment duration (days) | Total rats |
|---|---|---|---|---|
| 1 | Vehicle | 0 | 28 | 15 |
| 2 | TXA127 | 500 µg/kg | 28 | 15 |
| 3 | TXA127 | 1,000 µg/kg | 28 | 15 |
| 4 | TXA127 | 500 µg/kg* | 28 | 15 |
| 5 | PanCyte | 500 µg/kg* | 28 | 15 |
| 6 | PanCyte | 500 µg/kg | 28 | 15 |
| 7 | Linear PanCyte | 50 µg/kg* | 28 | 15 |

*rats treated by Alzet pump continuous administration subcutaneously

Animals were subjected to a modified Modified Neurological Rating Scale (mNRS) at 24 hours post reperfusion. Only animals with an overall score of ≥10 were included in this study. Animals were allocated into the test groups, according to the mNRS results on day 2, in order to have similar distribution of rats performance between groups. Starting on day 2, 24 hours post-surgery, animals in groups 4, 5 and 7 were implanted subcutaneously with an osmotic Alzet pump and treated with either 500 µg/kg TXA127 (SEQ ID NO:1), 500 µg/kg PanCyte (SEQ ID NO:22), or 50 µg/kg Linear PanCyte (SEQ ID NO:6). Animals in groups 2, 3 and 6 received 500 µg/kg or 1,000 µg/kg TXA127 or 500 µg/kg PanCyte, administered subcutaneously via daily injection. Animals in group 1 were treated with a daily subcutaneous injection of a PBS (vehicle).

Stepping Test (Evaluation Before Operation, Day 14, Day 21, Day 28, Day 35, Day 42 and Day 49)

Figure 5:
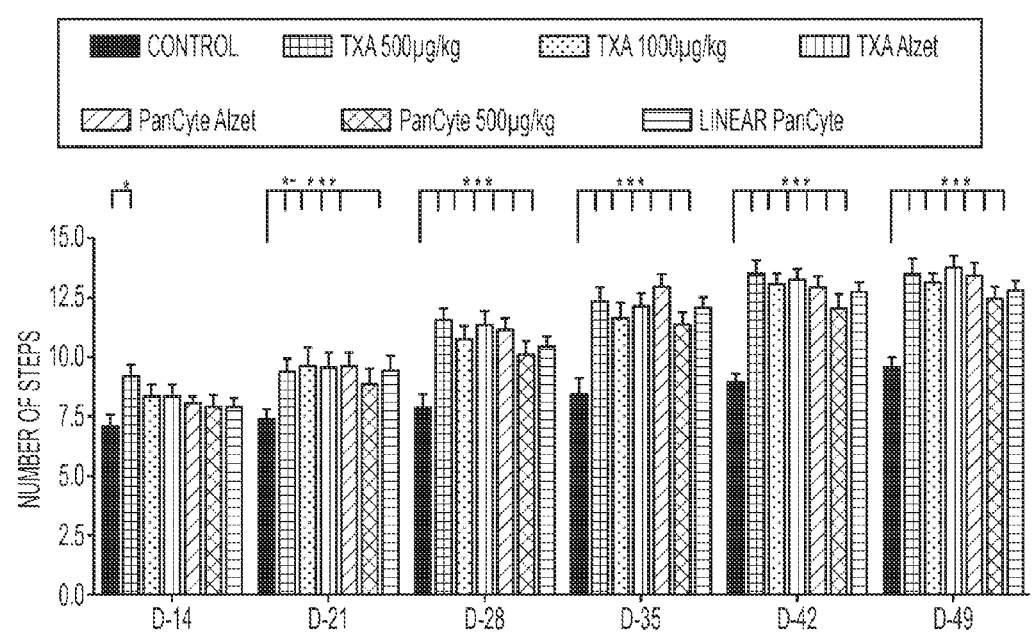
FIG. 5 shows an exemplary bar graph comparing the results of a step test administered on rats who received a transient middle cerebral arterial occlusion and either subcutaneously administered TXA127, PanCyte, or linear PanCyte for 28 days.

Animals were tested for forelimb akinesia in a stepping test (ST). The animal was held with its hind limbs fixed with one hand and the forelimb not to be monitored with the other, while the unrestrained fore-paw touches the table. The number of adjusting steps are counted while the animal is moved sideways along the table surface (85 cm in approximately five seconds), in the forehand & backhand direction for both forelimbs. FIG. 5 shows treatment with TXA127, PanCyte or Linear Pancyte significantly improved the performance of treated rats in all experimental conditions by Day 21 post-surgery, as compared to the vehicle control condition. A trend of improvement is observed as early as Day 14 post-surgery. It is of note that although only 50 ug/kg of Linear Pancyte was administered, the results are substantially equivalent to ten times as much TXA127 or PanCyte.

Forelimb Placement (Evaluation Before Operation, Day 14, Day 21, Day 28, Day 35, Day 42 and Day 49)

Figure 6:
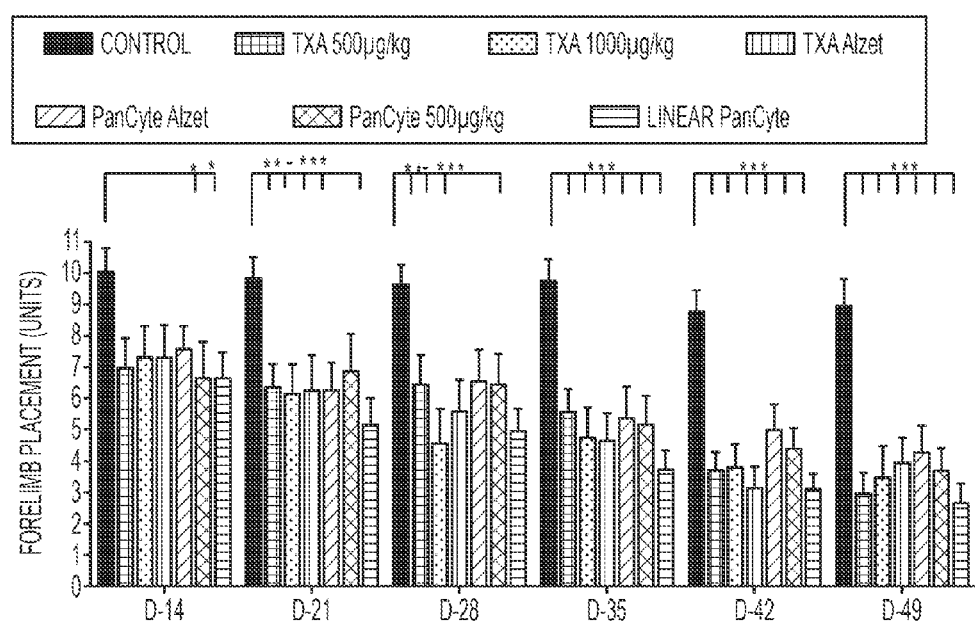
FIG. 6 shows an exemplary bar graph comparing the results of a forelimb placement test administered on rats who received a transient middle cerebral arterial occlusion and either subcutaneously administered TXA127, PanCyte, or linear PanCyte for 28 days.

For the forelimb-placing test, the rat was held close to a tabletop and the rat's ability to place the forelimb on the tabletop in response to whisker, visual, tactile, or proprioceptive stimulation was scored (0=normal, 12=maximally impaired). Scores were given in half-point increments (see below). Typically, there is a slow and steady recovery of limb placing behavior during the first month after stroke. FIG. 6 shows that significant improvement in performance was observed in all treatment conditions, as compared to vehicle control, beginning on Day 14 and continuing through the duration of the study. It again appears that the Linear PanCyte group had the best performance, particularly from Day 35 onward, despite being exposed to a far lower dose of agent than the other experimental groups were.

Body Swing (Evaluation Before Operation, Day 14, Day 21, Day 28, Day 35, Day 42 and Day 49)

Figure 7:
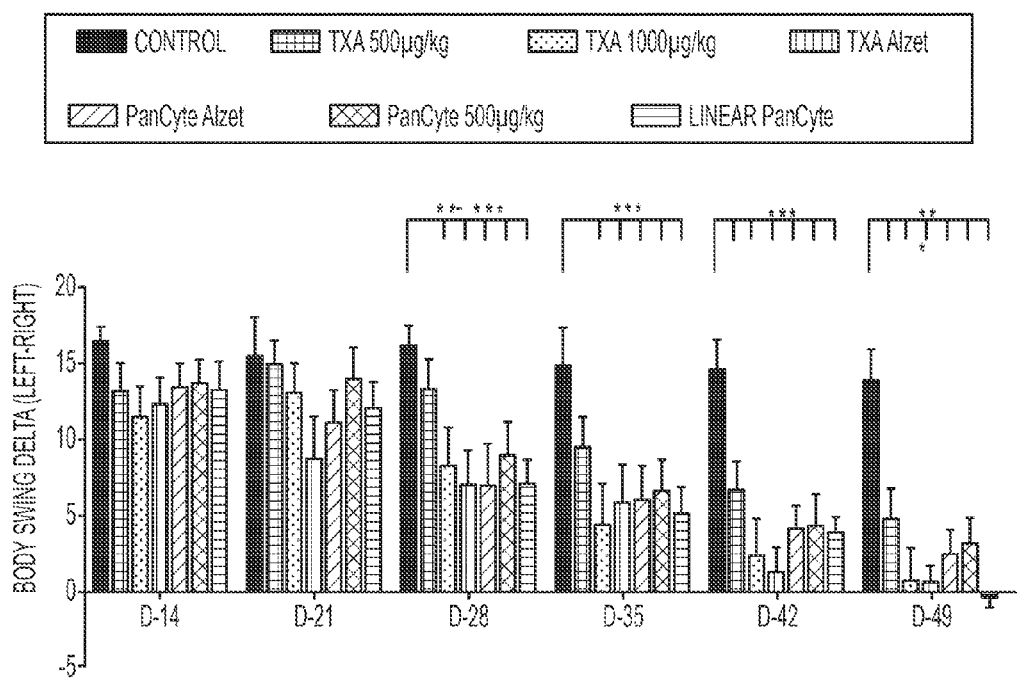
FIG. 7 shows an exemplary bar graph comparing the results of a body swing test administered on rats who received a transient middle cerebral arterial occlusion and either subcutaneously administered TXA127, PanCyte, or linear PanCyte for 28 days.

Each rat was held approximately one inch from the base of its tail. It was then elevated to an inch above a surface of a table. The rat was held in the vertical axis, defined as no more than 10° to either the left or the right side. A swing was recorded whenever the rat moves its head out of the vertical axis to either side. Before attempting another swing, the rat must return to the vertical position for the next swing to be counted. Twenty (20) total swings were counted. A normal rat typically has an equal number of swings to either side. Following focal ischemia, the rat tends to swing to the contralateral side (left side in this case). Body swing scores are expressed as a percentage of rightward over total swings. Often, there is a spontaneous partial recovery of body swing scores (toward 50%) during the first month after stroke. FIG. 7 shows that the 1,000 µg/kg TXA127, TXA Alzet, PanCyte Alzet, 500 µg/kg PanCyte, and Linear PanCyte groups all showed significant improvement in performance by Day 28, as compared to the vehicle control. The 500 µg/kg TXA127 group did not show significant results until Day 35. The 1,000 µg/kg TXA127, TXA Alzet, PanCyte Alzet, and Linear PanCyte groups all showed improvement by Day 21, and all experimental groups showed a trend toward improvement by Day 14. On Day 49, the TXA 1,000 µg/kg, TXA Alzet, and Linear PanCyte groups each appeared to perform at a near-normal (uninjured) level.

mNRS Evaluation (Evaluation Before Operation, Day 1, Day 14, Day 21, Day 28, Day 35, Day 42 and Day 49)

Figure 8:
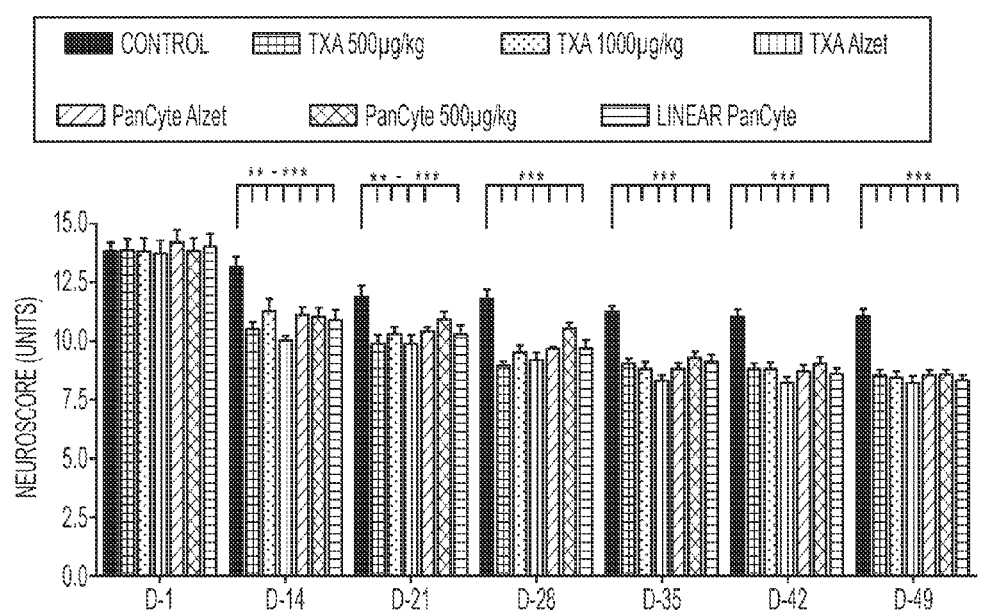
FIG. 8 shows an exemplary bar graph comparing the results of a neurological test (modified Neuroscore Scoring Scale) administered on rats who received a transient middle cerebral arterial occlusion and either subcutaneously administered TXA127, PanCyte, or linear PanCyte for 28 days.

The Modified Neurological Rating Scale (mNRS) was administered by an individual who was unaware of the drug/dose given (blind test). The mNRS as administered allows for neuro-scoring on a scale of 0 to 18 possible points. Animals with higher scores showed more severe symptoms and disability than lower scoring rats. FIG. 8 shows that each experimental group showed significant improvement in performance by Day 14, as compared to the vehicle control. The observed increased performance was maintained for the duration of the study.

Figure 9:
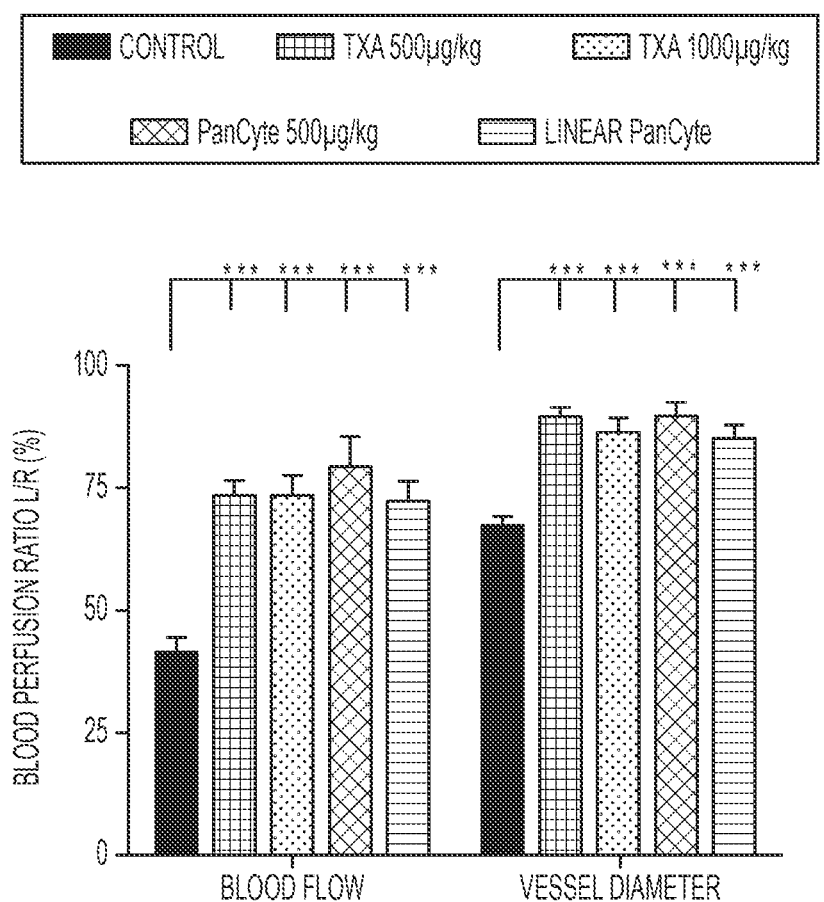
FIG. 9 shows an exemplary bar graph comparing the blood perfusion ratio between ipsilateral and contralateral sides, as well as blood vessel diameter, in animals subcutaneously administered TXA127, PanCyte, or linear PanCyte via injection for 28 days.

These results show that TXA127, PanCyte and Linear PanCyte are all strong therapeutic candidates with the ability to dramatically improve the performance of animals post-stroke. In addition to the performance benefits discussed above, blood flow and blood vessel diameter was measured using Laser Doppler, according to known protocols, in each non-Alzet group on Day 50. The results are shown in FIG. 9 and show that animals in all assessed treatment groups showed significantly increased blood vessel diameter and blood flow compared to control animals by Day 50. In particular, Linear PanCyte appears to have significantly improved therapeutic potential even beyond the other effective treatments tested in this example. These results are particularly surprising since the only difference between PanCyte and Linear PanCyte appears to be that PanCyte is cyclized, while Linear PanCyte is not. Cyclization of a peptide is typically thought to allow a peptide to be more effective in vivo by making it more resistant to protease degradation. Linear PanCyte, however, is almost equally effective at a lower dose of 50 µg/kg (as compared to 500 µg/kg of PanCyte) in this example.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of treating stroke comprising administering to a subject suffering from stroke a linear or cyclic angiotensin (1-7) peptide comprising the amino acid sequence $Asp^1$-$Arg^2$-$Val^3$-$Ser^4$-$Ile^5$-$His^6$-$Cys^7$ (SEQ ID NO:6) via systemic administration, wherein the systemic administration is not intracerebroventricular administration.

2. The method of claim 1, wherein the stroke is either ischemic stroke, hemorrhagic stroke, or a combination thereof.

3. The method of claim 1, wherein the linear or cyclic angiotensin (1-7) peptide is administered via continuous infusion.

4. The method of claim 1, wherein the linear or cyclic angiotensin (1-7) peptide is administered three times per month.

5. The method of claim 1, wherein the linear or cyclic angiotensin (1-7) peptide is administered twice per month.

6. The method of claim 1, wherein the linear or cyclic angiotensin (1-7) peptide is administered once per month.

7. The method of claim 1, wherein the linear or cyclic angiotensin (1-7) peptide is administered at an effective dose ranging from about 1-1,000 ug/kg/day.

8. The method of claim 1, wherein the linear or cyclic angiotensin (1-7) peptide is administered at an effective dose ranging from about 50-500 ug/kg/day.

9. The method of claim 1, wherein the linear or cyclic angiotensin (1-7) peptide is administered at an effective dose ranging from about 1-60 ug/kg/day.

10. The method of claim 1, wherein the functional equivalent angiotensin (1-7) peptide is a linear peptide.

11. The method of claim 1, wherein the angiotensin (1-7) peptide is a cyclic peptide.

12. The method of claim 11, wherein the cyclic peptide comprises a linkage between amino acids.

13. The method of claim 12, wherein the linkage is located at residues corresponding to positions $Ser^4$ and $Cys^7$ in SEQ ID NO: 6.

14. The method of claim 12, wherein the linkage is a thioether bridge.

15. The method of claim 1, wherein the linear or cyclic angiotensin (1-7) peptide comprises one or more chemical modifications to increase protease resistance, serum stability and/or bioavailability.

16. The method of claim 15, wherein the one or more chemical modifications comprise pegylation.

17. The method of claim 1, wherein the systemic administration is selected from intravenous administration, subcutaneous administration, inhalation, intradermal administration, transdermal administration, transmucosal administration, and/or oral administration.

18. The method of claim 17, wherein the systemic administration is intravenous administration.

19. The method of claim 17, wherein the systemic administration is subcutaneous administration.

20. The method of claim 1, wherein the linear or cyclic angiotensin (1-7) peptide is administered daily.

21. The method of claim 1, wherein the linear or cyclic angiotensin (1-7) peptide is administered twice daily.

* * * * *

UNITED STATES PATENT AND TRADEMARK OFFICE
CERTIFICATE OF CORRECTION

Page 1 of 1

PATENT NO. : 8,633,158 B1
APPLICATION NO. : 13/752202
DATED : January 21, 2014
INVENTOR(S) : Richard Franklin It is certified that error appears in the above-identified patent and that said Letters Patent is hereby corrected as shown below:

In the Claims:

Column 51, lines 65/66, correct claim 10 from:

"The method of claim 1, wherein the functional equivalent angiotensin (1-7) peptide is a linear peptide."

to read:

--The method of claim 1, wherein the angiotensin (1-7) peptide is a linear peptide.--

Signed and Sealed this
Twentieth Day of May, 2014

Michelle K. Lee
*Deputy Director of the United States Patent and Trademark Office*

```
                        SEQUENCE LISTING

<160> NUMBER OF SEQ ID NOS: 22

<210> SEQ ID NO 1
    <211> LENGTH: 7
    <212> TYPE: PRT
    <213> ORGANISM: Artificial Sequence
    <220> FEATURE:
    <223> OTHER INFORMATION: Chemically synthesized peptide

<400> SEQUENCE: 1

Asp Arg Val Tyr Ile His Pro
    1               5

<210> SEQ ID NO 2
    <211> LENGTH: 7
    <212> TYPE: PRT
    <213> ORGANISM: Artificial Sequence
    <220> FEATURE:
    <223> OTHER INFORMATION: Chemically synthesized peptide
    <220> FEATURE:
    <221> NAME/KEY: MISC_FEATURE
    <222> LOCATION: (4)..(4)
    <223> OTHER INFORMATION: homoserine

<400> SEQUENCE: 2

Asp Arg Val Xaa Ile His Cys
    1               5

<210> SEQ ID NO 3
    <211> LENGTH: 12
    <212> TYPE: PRT
    <213> ORGANISM: Artificial Sequence
    <220> FEATURE:
    <223> OTHER INFORMATION: Chemically synthesized peptide

<400> SEQUENCE: 3

Asp Arg Val Tyr Ile His Pro Phe His Leu Val Ile
    1               5                   10

<210> SEQ ID NO 4
    <211> LENGTH: 7
    <212> TYPE: PRT
    <213> ORGANISM: Artificial Sequence
    <220> FEATURE:
    <223> OTHER INFORMATION: Chemically synthesized peptide
    <220> FEATURE:
    <221> NAME/KEY: MISC_FEATURE
    <222> LOCATION: (1)..(1)
```

```
<223> OTHER INFORMATION: Any amino acid or dicarboxylic acid; Asp, Glu,
      Asn, Acpc (1-aminocyclopentane carboxylic acid), Ala, Me2Gly
      (N,N-dimethylglycine), Pro, Bet (betaine), Glu, Gly, Asp, Sar
      (sarcosine) or Suc (succinic acid)
<220> FEATURE:
<221> NAME/KEY: MISC_FEATURE
<222> LOCATION: (2)..(2)
<223> OTHER INFORMATION: Arg, Lys, Ala, Cit (citrulline), Orn
      (ornithine), acetylated Ser, Sar, D-Arg or D-Lys
<220> FEATURE:
<221> NAME/KEY: MISC_FEATURE
<222> LOCATION: (3)..(3)
<223> OTHER INFORMATION: Val, Ala, Leu, Nle (norleucine), Ile, Gly, Lys,
      Pro, HydroxyPro (hydroxyproline), Aib (2-aminoisobutyric acid),
      Acpc or Tyr
<220> FEATURE:
<221> NAME/KEY: MISC_FEATURE
<222> LOCATION: (4)..(4)
<223> OTHER INFORMATION: Tyr, Tyr(PO3), Thr, Ser, homoSer (homoserine),
      azaTyr (aza-alpha1-homo-L-tyrosine) or Ala
<220> FEATURE:
<221> NAME/KEY: MISC_FEATURE
<222> LOCATION: (5)..(5)
<223> OTHER INFORMATION: Ile, Ala, Leu, norLeu, Val or Gly
<220> FEATURE:
<221> NAME/KEY: MISC_FEATURE
<222> LOCATION: (6)..(6)
<223> OTHER INFORMATION: His, Arg or 6-NH2-Phe (6-aminophenylalaine)
<220> FEATURE:
<221> NAME/KEY: MISC_FEATURE
<222> LOCATION: (7)..(7)
<223> OTHER INFORMATION: Cys, Pro or Ala

<400> SEQUENCE: 4

Xaa Xaa Xaa Xaa Xaa Xaa Xaa
1               5

<210> SEQ ID NO 5
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (3)..(3)
<223> OTHER INFORMATION: Nle

<400> SEQUENCE: 5

Asp Arg Xaa Tyr Ile His Pro
1               5

<210> SEQ ID NO 6
<211> LENGTH: 7
<212> TYPE: PRT
<213> ORGANISM: Artificial Sequence
<220> FEATURE:
<223> OTHER INFORMATION: Chemically synthesized peptide

<400> SEQUENCE: 6

Asp Arg Val Ser Ile His Cys
1               5

<210> SEQ ID NO 7
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (4)..(4)
<223> OTHER INFORMATION: Tyr or Ser
<220> FEATURE:
```

```
<221> NAME/KEY: MISC_FEATURE
<222> LOCATION: (4)..(7)
<223> OTHER INFORMATION: 4,7-cyclization including thioether cyclization
<220> FEATURE:
<221> NAME/KEY: MISC_FEATURE
<222> LOCATION: (7)..(7)
<223> OTHER INFORMATION: Pro or Cys

<400> SEQUENCE: 7

Asp Arg Val Xaa Ile His Xaa
1               5

<210> SEQ ID NO 8
<211> LENGTH: 10
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (3)..(3)
<223> OTHER INFORMATION: Nle
<220> FEATURE:
<221> NAME/KEY: MISC_FEATURE
<222> LOCATION: (4)..(4)
<223> OTHER INFORMATION: Tyr or Ser
<220> FEATURE:
<221> NAME/KEY: MISC_FEATURE
<222> LOCATION: (4)..(7)
<223> OTHER INFORMATION: 4,7-cyclization including thioether cyclization
<220> FEATURE:
<221> NAME/KEY: MISC_FEATURE
<222> LOCATION: (7)..(7)
<223> OTHER INFORMATION: Pro or Cys

<400> SEQUENCE: 8

Asp Arg Xaa Xaa Ile His Xaa Phe His Leu
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (3)..(3)
<223> OTHER INFORMATION: Nle
<220> FEATURE:
<221> NAME/KEY: MISC_FEATURE
<222> LOCATION: (4)..(4)
<223> OTHER INFORMATION: Tyr or Ser
<220> FEATURE:
<221> NAME/KEY: MISC_FEATURE
<222> LOCATION: (4)..(7)
<223> OTHER INFORMATION: 4,7-cyclization including thioether cyclization
<220> FEATURE:
<221> NAME/KEY: MISC_FEATURE
<222> LOCATION: (7)..(7)
<223> OTHER INFORMATION: Pro or Cys

<400> SEQUENCE: 9

Asp Arg Xaa Xaa Ile His Xaa Phe
1               5

<210> SEQ ID NO 10
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
```

```
<222> LOCATION: (2)..(2)
<223> OTHER INFORMATION: Nle
<220> FEATURE:
<221> NAME/KEY: MISC_FEATURE
<222> LOCATION: (2)..(6)
<223> OTHER INFORMATION: 2,6-cyclization including thioether cyclization
<220> FEATURE:
<221> NAME/KEY: MISC_FEATURE
<222> LOCATION: (3)..(3)
<223> OTHER INFORMATION: Tyr or Ser
<220> FEATURE:
<221> NAME/KEY: MISC_FEATURE
<222> LOCATION: (6)..(6)
<223> OTHER INFORMATION: Pro or Cys

<400> SEQUENCE: 10

Arg Xaa Xaa Ile His Xaa Phe
1               5

<210> SEQ ID NO 11
<211> LENGTH: 6
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Nle
<220> FEATURE:
<221> NAME/KEY: MISC_FEATURE
<222> LOCATION: (2)..(2)
<223> OTHER INFORMATION: Tyr or Ser
<220> FEATURE:
<221> NAME/KEY: MISC_FEATURE
<222> LOCATION: (2)..(5)
<223> OTHER INFORMATION: 2,5-cyclization including thioether cyclization
<220> FEATURE:
<221> NAME/KEY: MISC_FEATURE
<222> LOCATION: (5)..(5)
<223> OTHER INFORMATION: Pro or Cys

<400> SEQUENCE: 11

Xaa Xaa Ile His Xaa Phe
1               5

<210> SEQ ID NO 12
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (3)..(3)
<223> OTHER INFORMATION: Nle
<220> FEATURE:
<221> NAME/KEY: MISC_FEATURE
<222> LOCATION: (4)..(4)
<223> OTHER INFORMATION: Tyr or Ser
<220> FEATURE:
<221> NAME/KEY: MISC_FEATURE
<222> LOCATION: (4)..(7)
<223> OTHER INFORMATION: 4,7-cyclization including thioether cyclization
<220> FEATURE:
<221> NAME/KEY: MISC_FEATURE
<222> LOCATION: (7)..(7)
<223> OTHER INFORMATION: Pro or Cys

<400> SEQUENCE: 12

Asp Arg Xaa Xaa Ile His Xaa
1               5

<210> SEQ ID NO 13
```

```
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (3)..(3)
<223> OTHER INFORMATION: Nle
<220> FEATURE:
<221> NAME/KEY: MISC_FEATURE
<222> LOCATION: (4)..(4)
<223> OTHER INFORMATION: Tyr or Ser
<220> FEATURE:
<221> NAME/KEY: MISC_FEATURE
<222> LOCATION: (4)..(7)
<223> OTHER INFORMATION: 4,7-cyclization including thioether cyclization
<220> FEATURE:
<221> NAME/KEY: MISC_FEATURE
<222> LOCATION: (7)..(7)
<223> OTHER INFORMATION: Pro or Cys

<400> SEQUENCE: 13

Asp Arg Xaa Xaa Ile His Xaa Phe His
1               5

<210> SEQ ID NO 14
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Any amino acid, but typically a negatively-
      charged amino acid such as Glu or Asp
<220> FEATURE:
<221> NAME/KEY: MISC_FEATURE
<222> LOCATION: (2)..(2)
<223> OTHER INFORMATION: Any positively-charged amino acid such as Arg
      or Lys
<220> FEATURE:
<221> NAME/KEY: MISC_FEATURE
<222> LOCATION: (3)..(3)
<223> OTHER INFORMATION: Any aliphatic amino acid, such as Leu, Ile or
      Val
<220> FEATURE:
<221> NAME/KEY: MISC_FEATURE
<222> LOCATION: (4)..(4)
<223> OTHER INFORMATION: D-stereoisomer or L-stereoisomer
<220> FEATURE:
<221> NAME/KEY: MISC_FEATURE
<222> LOCATION: (4)..(4)
<223> OTHER INFORMATION: Abu (2-aminobutyric acid), Ala, Tyr or Ser
<220> FEATURE:
<221> NAME/KEY: MISC_FEATURE
<222> LOCATION: (4)..(7)
<223> OTHER INFORMATION: 4,7-cyclization including thioether cyclization
<220> FEATURE:
<221> NAME/KEY: MISC_FEATURE
<222> LOCATION: (5)..(5)
<223> OTHER INFORMATION: Any aliphatic amino acid, such as Leu, Ile or
      Val
<220> FEATURE:
<221> NAME/KEY: MISC_FEATURE
<222> LOCATION: (6)..(6)
<223> OTHER INFORMATION: His
<220> FEATURE:
<221> NAME/KEY: MISC_FEATURE
<222> LOCATION: (6)..(6)
<223> OTHER INFORMATION: His
<220> FEATURE:
<221> NAME/KEY: MISC_FEATURE
<222> LOCATION: (7)..(7)
<223> OTHER INFORMATION: D-stereoisomer or L-stereoisomer
<220> FEATURE:
<221> NAME/KEY: MISC_FEATURE
```

```
<222> LOCATION: (7)..(7)
<223> OTHER INFORMATION: Abu (2-aminobutyric acid), Ala, Pro or Cys

<400> SEQUENCE: 14

Xaa Xaa Xaa Xaa Xaa Xaa Xaa
1               5

<210> SEQ ID NO 15
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (4)..(4)
<223> OTHER INFORMATION: Abu (2-aminobutyric acid)

<400> SEQUENCE: 15

Asp Arg Val Xaa Ile His Ala
1               5

<210> SEQ ID NO 16
<211> LENGTH: 7
<212> TYPE: PRT
<213> ORGANISM: Artificial Sequence
<220> FEATURE:
<223> OTHER INFORMATION: Chemically synthesized peptide

<400> SEQUENCE: 16

Asp Arg Val Ala Ile His Ala
1               5

<210> SEQ ID NO 17
<211> LENGTH: 10
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Any amino acid, but typically a negatively
      charged amino acid such as Glu or Asp
<220> FEATURE:
<221> NAME/KEY: MISC_FEATURE
<222> LOCATION: (2)..(2)
<223> OTHER INFORMATION: Any positively charged amino acid such as Arg
      or Lys
<220> FEATURE:
<221> NAME/KEY: MISC_FEATURE
<222> LOCATION: (3)..(3)
<223> OTHER INFORMATION: Nle
<220> FEATURE:
<221> NAME/KEY: MISC_FEATURE
<222> LOCATION: (4)..(4)
<223> OTHER INFORMATION: D-stereoisomer or L-stereoisomer
<220> FEATURE:
<221> NAME/KEY: MISC_FEATURE
<222> LOCATION: (4)..(4)
<223> OTHER INFORMATION: Abu (2-aminobutyric acid), Ala, Tyr or Ser
<220> FEATURE:
<221> NAME/KEY: MISC_FEATURE
<222> LOCATION: (4)..(7)
<223> OTHER INFORMATION: 4,7-cyclization including thioether cyclization
<220> FEATURE:
<221> NAME/KEY: MISC_FEATURE
<222> LOCATION: (5)..(5)
<223> OTHER INFORMATION: Any aliphatic amino acid, such as Leu, Nle, Ile
      or Val
<220> FEATURE:
<221> NAME/KEY: MISC_FEATURE
<222> LOCATION: (6)..(6)
<223> OTHER INFORMATION: His
```

```
<220> FEATURE:
<221> NAME/KEY: MISC_FEATURE
<222> LOCATION: (7)..(7)
<223> OTHER INFORMATION: D-stereoisomer or L-stereoisomer
<220> FEATURE:
<221> NAME/KEY: MISC_FEATURE
<222> LOCATION: (7)..(7)
<223> OTHER INFORMATION: Abu (2-aminobutyric acid), Ala, Pro or Cys
<220> FEATURE:
<221> NAME/KEY: MISC_FEATURE
<222> LOCATION: (8)..(8)
<223> OTHER INFORMATION: Any amino acid other than Pro, typically Phe or
      Ile
<220> FEATURE:
<221> NAME/KEY: MISC_FEATURE
<222> LOCATION: (9)..(9)
<223> OTHER INFORMATION: His
<220> FEATURE:
<221> NAME/KEY: MISC_FEATURE
<222> LOCATION: (10)..(10)
<223> OTHER INFORMATION: Any aliphatic residue, such as Ile, Val or Leu

<400> SEQUENCE: 17

Xaa Xaa Xaa Xaa Xaa Xaa Xaa Xaa Xaa Xaa
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (3)..(3)
<223> OTHER INFORMATION: Nle
<220> FEATURE:
<221> NAME/KEY: MISC_FEATURE
<222> LOCATION: (4)..(4)
<223> OTHER INFORMATION: Abu (2-aminobutyric acid)

<400> SEQUENCE: 18

Asp Arg Xaa Xaa Ile His Ala
1               5

<210> SEQ ID NO 19
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (3)..(3)
<223> OTHER INFORMATION: Nle

<400> SEQUENCE: 19

Asp Arg Xaa Ala Ile His Ala
1               5

<210> SEQ ID NO 20
<211> LENGTH: 8
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (3)..(3)
<223> OTHER INFORMATION: Nle
<220> FEATURE:
<221> NAME/KEY: MISC_FEATURE
<222> LOCATION: (4)..(4)
<223> OTHER INFORMATION: Abu (2-aminobutyric acid)
```

```
-continued

<400> SEQUENCE: 20

Asp Arg Xaa Xaa Ile His Ala Ile
1               5

<210> SEQ ID NO 21
<211> LENGTH: 8
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (3)..(3)
<223> OTHER INFORMATION: Nle

<400> SEQUENCE: 21

Asp Arg Xaa Ala Ile His Ala Ile
1               5

<210> SEQ ID NO 22
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (4)..(7)
<223> OTHER INFORMATION: 4,7-cyclization including thioether cyclization

<400> SEQUENCE: 22

Asp Arg Val Ser Ile His Cys
1               5
```